US012778380B2

(12) United States Patent
Watanabe

(10) Patent No.: US 12,778,380 B2
(45) Date of Patent: Nov. 3, 2026

(54) IMAGE PROCESSING DEVICE, ENDOSCOPE SYSTEM, AND METHOD OF OPERATING IMAGE PROCESSING DEVICE

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 946 days.

(21) Appl. No.: 17/656,162

(22) Filed: Mar. 23, 2022

(65) Prior Publication Data

US 2022/0211251 A1 Jul. 7, 2022

Related U.S. Application Data

(63) Continuation of application No. PCT/JP2020/035329, filed on Sep. 17, 2020.

(30) Foreign Application Priority Data

Sep. 27, 2019 (JP) ................................ 2019-177808

(51) Int. Cl.
*G06T 7/90* (2017.01)
*A61B 1/00* (2006.01)
(Continued)

(52) U.S. Cl.
CPC ...... *A61B 1/000094* (2022.02); *A61B 1/0653* (2013.01); *A61B 5/02042* (2013.01);
(Continued)

(58) Field of Classification Search
CPC ........... A61B 1/000094; A61B 1/0653; A61B 1/00188; A61B 1/043; A61B 1/0638;
(Continued)

(56) References Cited

U.S. PATENT DOCUMENTS 8,994,801 B2 3/2015 Tanaka et al.
2010/0097454 A1 4/2010 Kubo et al.
(Continued)

FOREIGN PATENT DOCUMENTS

CN 105266750 A 1/2016
JP 2007-020728 A 2/2007
(Continued)

OTHER PUBLICATIONS

R. N. Kacmaz and B. Yilmaz, "Detection of Ulcerative Colitis From Colonoscopy Images," 2018 Medical Technologies National Congress (TIPTEKNO), Magusa, Cyprus, 2018, pp. 1-4, doi: 10.1109/TIPTEKNO.2018.8596841. (Year: 2018).*
(Continued)

*Primary Examiner* — Patrick Fernandes
*Assistant Examiner* — Melissa Jo Montgomery
(74) *Attorney, Agent, or Firm* — Studebaker Brackett PLLC

(57) ABSTRACT

A switching determination index value (red feature quantity), which is used to determine whether or not to switch a first observation environment to a second observation environment in which an object to be observed is enlarged at a second magnification ratio higher than a first magnification ratio is calculated on the basis of a first medical image that is obtained in the first observation environment in which the object to be observed is enlarged at the first magnification ratio. Whether or not to switch the first observation environment to the second observation environment is determined on the basis of the switching determination index value. The first observation environment is switched to the second observation environment by a specific operation in a case where it is determined that switching to the second observation environment is to be performed.

10 Claims, 18 Drawing Sheets

(51) Int. Cl.

| | |
|---|---|
| ***A61B 1/045*** | (2006.01) |
| ***A61B 1/06*** | (2006.01) |
| ***A61B 5/02*** | (2006.01) |
| ***G06T 7/00*** | (2017.01) |

(52) U.S. Cl.
CPC .............. *G06T 7/0012* (2013.01); *G06T 7/90* (2017.01); *A61B 1/045* (2013.01); *G06T 2207/10068* (2013.01); *G06T 2207/30028* (2013.01); *G06T 2207/30101* (2013.01)

(58) Field of Classification Search
CPC ......... A61B 1/045; A61B 1/0655; A61B 1/04; A61B 1/00045; A61B 1/06; A61B 5/02042; A61B 1/0188; G06T 7/0012; G06T 7/90; G06T 2207/10068; G06T 2207/30028; G06T 2207/30101; H04N 7/18
See application file for complete search history.

(56) References Cited

U.S. PATENT DOCUMENTS

| | | | |
|---|---|---|---|
| 2012/0190922 A1 | 7/2012 | Kaku | |
| 2012/0302847 A1 | 11/2012 | Ozawa et al. | |
| 2015/0379698 A1 | 12/2015 | Kuramoto et al. | |
| 2017/0004620 A1* | 1/2017 | Kitamura | G06T 7/0016 |
| 2018/0214004 A1* | 8/2018 | Kamon | A61B 5/14552 |
| 2019/0069769 A1* | 3/2019 | Kubo | A61B 1/0638 |
| 2020/0242764 A1 | 7/2020 | Aoyama | |

FOREIGN PATENT DOCUMENTS

| | | | | |
|---|---|---|---|---|
| JP | 2010-142546 A | 7/2010 | |
| JP | 2012-239816 A | 12/2012 | |
| WO | 2013/140667 A1 | 9/2013 | |
| WO | WO-2018225448 A1 * | 12/2018 | A61B 1/00009 |
| WO | 2019/078204 A1 | 4/2019 | |
| WO | 2019/142689 A1 | 7/2019 | |

OTHER PUBLICATIONS

International Search Report issued in PCT/JP2020/035329; mailed Oct. 27, 2020.

Written Opinion of the International Searching Authority issued in PCT/JP2020/035329; mailed Oct. 27, 2020.

An Office Action; mailed by the China National Intellectual Property Administration of the People's Republic of China on Oct. 17, 2024, which corresponds to Chinese Patent Application No. 202080066978.1 and is related to U.S. Appl. No. 17/656,162.

The extended European search report issued by the European Patent Office on Oct. 21, 2022, which corresponds to European Patent Application No. 20868395.3-1126 and is related to U.S. Appl. No. 17/656,162.

An Office Action mailed by China National Intellectual Property Administration on May 30, 2025, which corresponds to Chinese Patent Application No. 202080066978.1 and is related to U.S. Appl. No. 17/656,162; with English language translation.

An Office Action mailed by China National Intellectual Property Administration on Feb. 27, 2025, which corresponds to Chinese Patent Application No. 202080066978.1 and is related to U.S. Appl. No. 17/656,162; with English language translation.

* cited by examiner

IMAGE PROCESSING DEVICE, ENDOSCOPE SYSTEM, AND METHOD OF OPERATING IMAGE PROCESSING DEVICE

CROSS-REFERENCE TO RELATED APPLICATIONS

This application is a Continuation of PCT International Application No. PCT/JP2020/035329 filed on 17 Sep. 2020, which claims priority under 35 U.S.C § 119(a) to Japanese Patent Application No. 2019-177808 filed on 27 Sep. 2019. The above application is hereby expressly incorporated by reference, in its entirety, into the present application.

BACKGROUND OF THE INVENTION

1. Field of the Invention

The present invention relates to an image processing device, an endoscope system, and a method of operating image processing device that perform processing related to a disease, such as ulcerative colitis.

2. Description of the Related Art

In a medical field, a diagnosis is widely made using a medical image. For example, there is an endoscope system that comprises a light source device, an endoscope, and a processor device as an apparatus using a medical image. In the endoscope system, an object to be observed is irradiated with illumination light and a medical image is acquired from the image pickup of the object to be observed illuminated with the illumination light. The medical image is displayed on a display and is used for diagnosis.

Further, in the diagnosis using an endoscope, an image suitable for an observation environment is displayed on the display depending on the type of illumination light or image processing. For example, in JP2012-239816A (corresponding to US2012/0302847A1), the display of the display is switched to an oxygen saturation image from a normal light image in which blood vessels are emphasized in a case where a hypoxic state is made under a situation where oxygen saturation is measured on the basis of the medical image. A user easily diagnoses a lesion area by observing the oxygen saturation displayed on the display.

SUMMARY OF THE INVENTION

Further, disease state processing, which is related to the state of a disease, for performing suitable image processing on an endoscopic image to determine the stage of a disease has been developed in recent years. In order to reliably perform the disease state processing, a feature in a medical image needs to highly correlate with the feature of a pathological examination that is correct in regard to the determination of the state of a disease. However, since the feature of the pathological examination does not necessarily appear in the medical image, an observation environment, such as the spectrum of illumination light or the magnification ratio of the object to be observed, is changed to make a feature, which highly correlates with the pathological examination, appear in the medical image. Accordingly, it has been required to set an observation environment in which a feature highly correlating with a pathological examination can be found in an endoscopic image during an endoscopy.

An object of the present invention is to provide an image processing device, an endoscope system, and a method of operating image processing device that can set an observation environment in which a feature highly correlating with a pathological examination is found in a medical image.

An image processing device according to an aspect of the present invention comprises a processor. The processor calculates a switching determination index value, which is used to determine whether or not to switch a first observation environment to a second observation environment in which an object to be observed is enlarged at a second magnification ratio higher than a first magnification ratio, on the basis of a first medical image that is obtained from image pickup of the object to be observed in the first observation environment in which the object to be observed is enlarged at the first magnification ratio; determines whether or not to switch the first observation environment to the second observation environment on the basis of the switching determination index value; and sets a magnification ratio of the object to be observed to the second magnification ratio by a specific operation and switches the first observation environment to the second observation environment in a case where it is determined that switching to the second observation environment is to be performed.

It is preferable that the switching determination index value is a red feature quantity representing a red component of the object to be observed. It is preferable that the processor determines that switching to the second observation environment is not to be performed in a case where the red feature quantity is smaller than a lower limit of a red feature quantity range or a case where the red feature quantity is equal to or larger than an upper limit of the red feature quantity range, and determines that switching to the second observation environment is to be performed in a case where the red feature quantity is in the red feature quantity range.

It is preferable that the first observation environment includes illuminating the object to be observed with normal light or special light or displaying a color difference-expanded image in which a color difference in a plurality of ranges to be observed of the object to be observed expands on a display, and the second observation environment includes illuminating the object to be observed with special light. It is preferable that the first magnification ratio is less than 60 times and the second magnification ratio is 60 times or more.

It is preferable that the processor performs disease state processing, which is related to a state of a disease, on the basis of a second medical image obtained from image pickup of the object to be observed in the second observation environment, and the disease state processing includes at least one of calculating an index value related to a stage of the disease, determining the stage of the disease, or determining whether or not the disease has pathologically remitted on the basis of the second medical image.

It is preferable that the processor calculates a bleeding index value, which represents a degree of bleeding of the object to be observed, or a degree of irregularity of superficial blood vessels, and determines whether or not the disease has pathologically remitted on the basis of the bleeding index value or the degree of irregularity of the superficial blood vessels. It is preferable that the processor determines that the disease has pathologically remitted in a case where the bleeding index value is equal to or smaller than a threshold value for bleeding and the degree of irregularity of the superficial blood vessels is equal to or smaller than a threshold value for the degree of irregularity, and determines that the disease has not pathologically remitted in a case where any one of a condition in which the bleeding index value exceeds the threshold value for bleeding or a condition in which the degree of irregularity of the superficial blood vessels exceeds the threshold value for the degree of irregularity is satisfied.

It is preferable that the bleeding index value is the number of pixels having pixel values equal to or smaller than a threshold value for blue in a blue image of the second medical image, and the degree of irregularity is the number of pixels of a region in which a density of the superficial blood vessels included in the second medical image is equal to or higher than a threshold value for density. It is preferable that the specific operation includes a user's operation performed according to a notification that promotes switching to the second observation environment, or automatic switching to the second observation environment. It is preferable that the disease is ulcerative colitis.

An endoscope system according to another aspect of the present invention comprises an endoscope which illuminates an object to be observed and picks up an image of the object to be observed and of which a magnification ratio of the object to be observed is adjustable, and a processor device that includes a processor. The processor calculates a switching determination index value, which is used to determine whether or not to switch a first observation environment to a second observation environment in which the object to be observed is enlarged at a second magnification ratio higher than a first magnification ratio, on the basis of a first medical image that is obtained from the endoscope in the first observation environment in which the object to be observed is enlarged at the first magnification ratio; determines whether or not to switch the first observation environment to the second observation environment on the basis of the switching determination index value; and sets a magnification ratio of the object to be observed to the second magnification ratio by a specific operation and switches the first observation environment to the second observation environment in a case where it is determined that switching to the second observation environment is to be performed.

A method of operating an image processing device according to still another aspect of the present invention comprises: a step of calculating a switching determination index value, which is used to determine whether or not to switch a first observation environment to a second observation environment in which an object to be observed is enlarged at a second magnification ratio higher than a first magnification ratio, on the basis of a first medical image that is obtained from image pickup of the object to be observed in the first observation environment in which the object to be observed is enlarged at the first magnification ratio; a step of determining whether or not to switch the first observation environment to the second observation environment on the basis of the switching determination index value; and a step of setting a magnification ratio of the object to be observed to the second magnification ratio by a specific operation and switching the first observation environment to the second observation environment in a case where it is determined that switching to the second observation environment is to be performed.

According to the present invention, it is possible to set an observation environment in which a feature highly correlating with a pathological examination is found in a medical image.

DESCRIPTION OF THE PREFERRED EMBODIMENTS

First Embodiment

Figure 1:
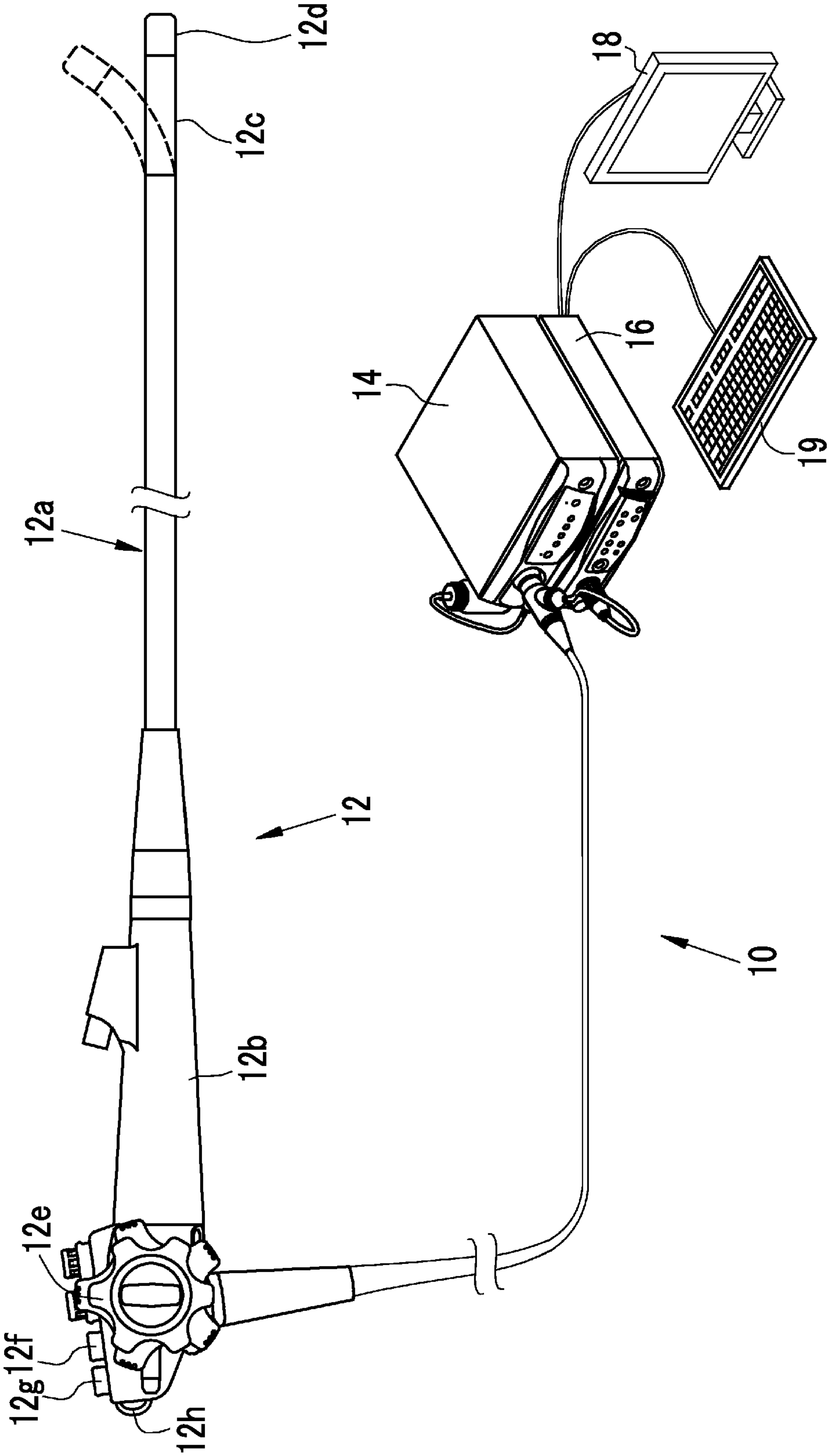
FIG. 1 is a diagram showing the appearance of an endoscope system.

In FIG. 1, an endoscope system 10 includes an endoscope 12, a light source device 14, a processor device 16, a display 18, and a user interface 19. The endoscope 12 is optically connected to the light source device 14, and is electrically connected to the processor device 16. The endoscope 12 includes an insertion part 12*a* that is to be inserted into the body of an object to be observed, an operation part 12*b* that is provided at the proximal end portion of the insertion part 12*a*, and a bendable part 12*c* and a distal end part 12*d* that are provided on the distal end side of the insertion part 12*a*. In a case where angle knobs 12*e* of the operation part 12*b* are operated, the bendable part 12*c* is operated to be bent. As the bendable part 12*c* is operated to be bent, the distal end part 12*d* is made to face in a desired direction.

Further, the operation part 12*b* is provided with a mode changeover switch (SW) 12*f* that is used for an operation for switching a mode, a static image-acquisition instruction part 12*g* that is used for an instruction to acquire the static image of the object to be observed, and a zoom operation part 12*h* that is used for the operation of a zoom lens 43 (see FIG. 2), in addition to the angle knobs 12*e*.

The endoscope system 10 has three modes, that is, a normal light mode, a special light mode, and a disease-related processing mode. In the normal light mode, the object to be observed is illuminated with normal light and the image of the object to be observed is picked up, so that a normal light image having a natural hue is displayed on the display 18. In the special light mode, a special light image obtained on the basis of special light having a wavelength range different from the wavelength range of normal light is displayed on the display 18. The special light image includes a color difference-expanded image that is subjected to color difference expansion processing for expanding a color difference in a plurality of ranges to be observed of the object to be observed. In the disease-related processing mode, it is determined whether or not ulcerative colitis has pathologically remitted. In the disease-related processing mode, an index value related to the stage of ulcerative colitis may be calculated or the stage of ulcerative colitis may be determined.

Medical images, such as a radiation image obtained from a radiographic device, a CT image obtained from computed tomography (CT), and a MRI image obtained from magnetic resonance imaging (MRI), may be used as an image, which is used in the disease-related processing mode, in addition to the special light image as an endoscopic image that is one of medical images. Further, the processor device 16 to which the endoscope 12 is connected corresponds to an image processing device according to an embodiment of the present invention and the disease-related processing mode is performed in the processor device 16, but the disease-related processing mode may be performed by other methods. For example, an external image processing device separate from the endoscope system 10 may be provided with the function of a disease-related processing unit 66, a medical image may be input to the external image processing device to perform the disease-related processing mode, and the result of the disease-related processing mode may be displayed on an external display connected to the external image processing device.

The processor device 16 is electrically connected to the display 18 and the user interface 19. The display 18 outputs and displays the image of the object to be observed, information attached to the image of the object to be observed, and the like. The user interface 19 has a function to receive an input operation, such as function settings. An external recording unit (not shown), which records images, image information, and the like, may be connected to the processor device 16. Further, the processor device 16 corresponds to an image processing device of the present invention.

Figure 2:
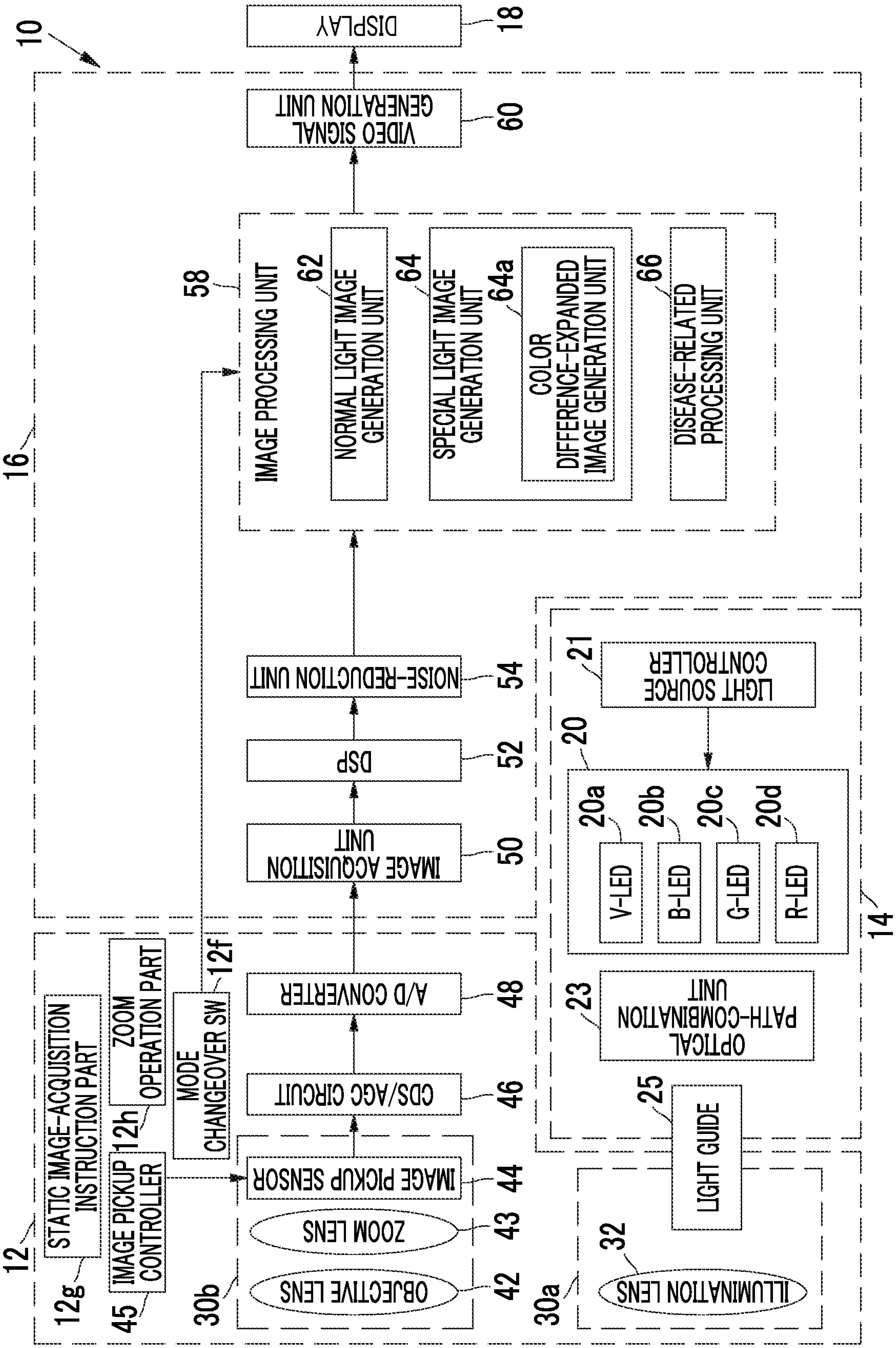
FIG. 2 is a block diagram showing the functions of an endoscope system according to a first embodiment.

In FIG. 2, the light source device 14 comprises a light source unit 20 and a light source controller 21 that controls the light source unit 20. The light source unit 20 includes, for example, a plurality of semiconductor light sources, turns on or off each of these semiconductor light sources, and emits illumination light, which illuminates the object to be observed, by controlling the amount of light from each semiconductor light source in a case where each semiconductor light source is turned on. In this embodiment, the light source unit 20 includes four color LEDs, that is, a violet light emitting diode (V-LED) 20*a*, a blue light emitting diode (B-LED) 20*b*, a green light emitting diode (G-LED) 20*c*, and a red light emitting diode (R-LED) 20*d*.

Figure 3:
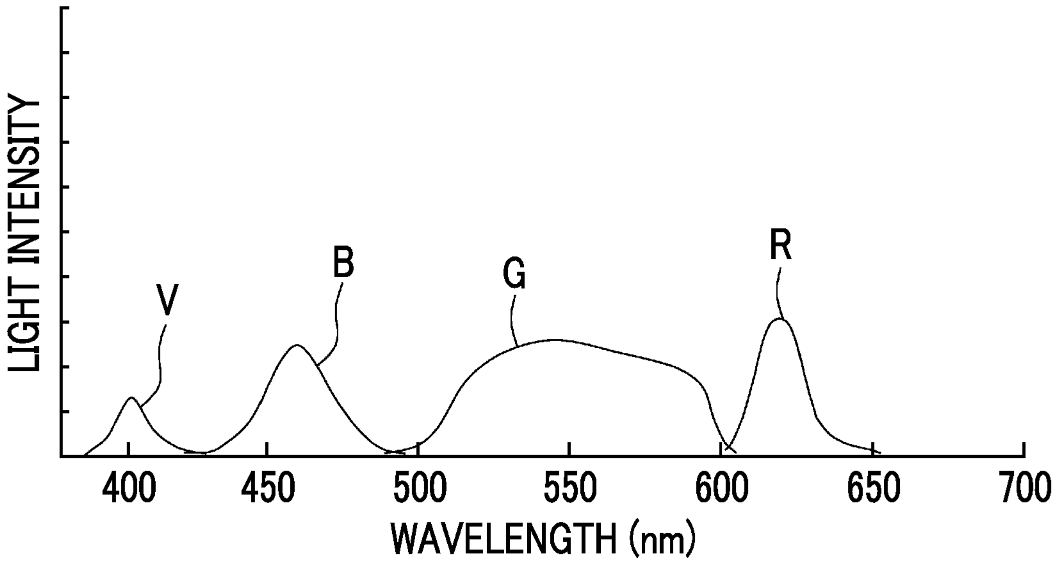
FIG. 3 is a graph showing the spectra of violet light V, blue light B, green light G, and red light R.

As shown in FIG. 3, the V-LED 20*a* generates violet light V of which the central wavelength is in the range of 405±10 nm and the wavelength range is in the range of 380 to 420 nm. The B-LED 20*b* generates blue light B of which the central wavelength is in the range of 460±10 nm and the wavelength range is in the range of 420 to 500 nm. The G-LED 20*c* generates green light G of which the wavelength range is in the range of 480 to 600 nm. The R-LED 20*d* generates red light R of which the central wavelength is in the range of 620 to 630 nm and the wavelength range is in the range of 600 to 650 nm.

The light source controller 21 controls the V-LED 20*a*, the B-LED 20*b*, the G-LED 20*c*, and the R-LED 20*d*. Further, the light source controller 21 controls the respective LEDs 20*a* to 20*d* so that normal light of which the light intensity ratios of violet light V, blue light B, green light G, and red light R are Vc:Bc:Gc:Rc is emitted in the normal light mode.

Figure 4:
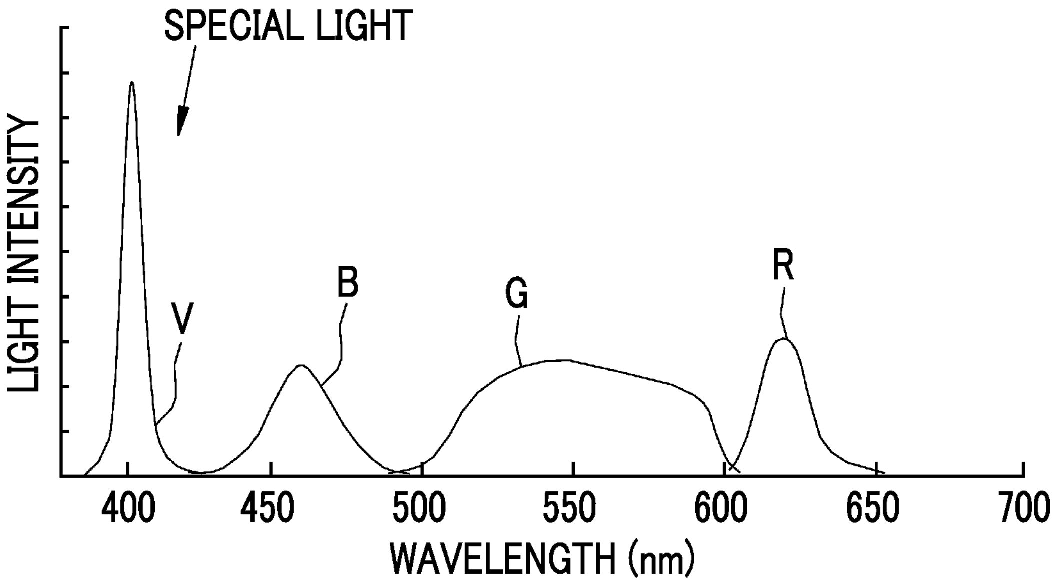
FIG. 4 is a graph showing the spectrum of special light of the first embodiment.
Figure 5:
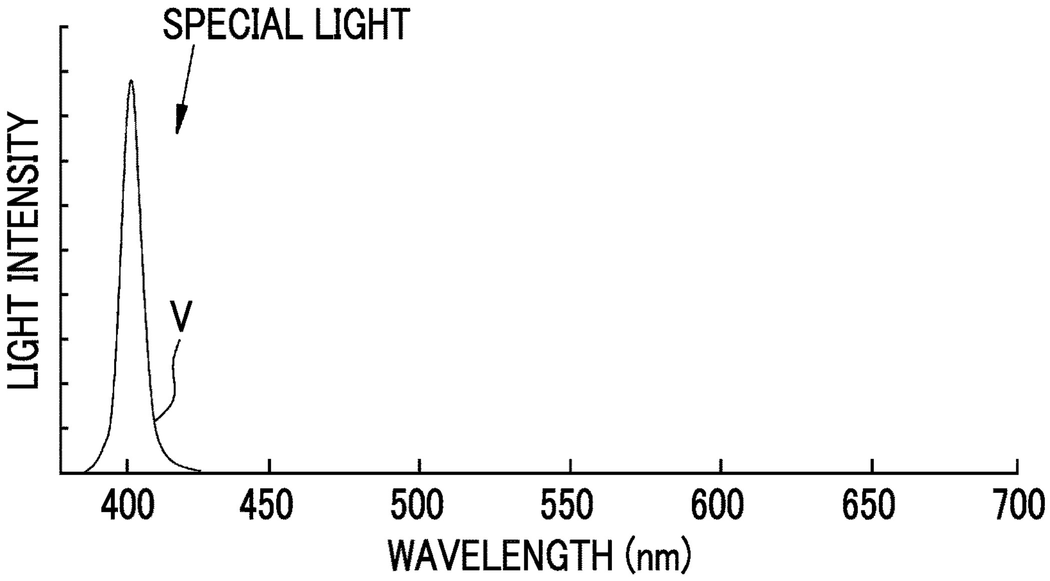
FIG. 5 is a graph showing the spectrum of special light that includes only violet light V.

Furthermore, the light source controller 21 controls the respective LEDs 20*a* to 20*d* so that special light of which the light intensity ratios of violet light V as narrow-band light having a short wavelength, blue light B, green light G, and red light R are Vs:Bs:Gs:Rs is emitted in the special light mode. It is preferable that special light having the light intensity ratios Vs:Bs:Gs:Rs emphasizes superficial blood vessels and the like. For this purpose, it is preferable that the light intensity of violet light V of special light is made higher than the light intensity of blue light B thereof. For example, as shown in FIG. 4, a ratio of the light intensity Vs of violet light V to the light intensity Bs of blue light B is set to “4:1”. Further, as shown in FIG. 5, special light may be adapted so that the light intensity ratios of violet light V, blue light B, green light G, and red light R are set to 1:0:0:0 and only violet light V as narrow-band light having a short wavelength is emitted.

Further, in the disease-related processing mode, the light source controller 21 illuminates the object to be observed with any one of normal light or special light in a first observation environment in which the object to be observed is enlarged at a first magnification ratio and illuminates the object to be observed with special light in a second observation environment in which the object to be observed is enlarged at a second magnification ratio higher than the first magnification ratio. Accordingly, in a case where a switching determination unit 87 (see FIG. 15) determines whether or not to switch the first observation environment to the second observation environment, the light source controller 21 performs a control to switch illumination light, which illuminates the object to be observed, to special light from normal light or special light. In this embodiment, in the first observation environment, the object to be observed is illuminated with special light and a color difference-expanded image is displayed on the display 18 as the special light image. However, in the first observation environment, the object to be observed may be illuminated with normal light and a normal light image may be displayed on the display 18. Furthermore, in the second observation environment, the object to be observed may be illuminated with normal light and a normal light image may be displayed on the display 18. A user selects the type of illumination light or the type of an image to be displayed on the display 18 in the first observation environment or the second observation environment by selectively operating an observation environment selection unit (not shown), which is provided in the processor device 16, according to an operation using the user interface 19.

In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Light emitted from each of the LEDs 20*a* to 20*d* is incident on a light guide 25 through an optical path-combination unit 23 that is composed of a mirror, a lens, and the like. The light guide 25 is built in the endoscope 12 and a universal cord (a cord connecting the endoscope 12 to the light source device 14 and the processor device 16). The light guide 25 transmits light, which is emitted from the optical path-combination unit 23, to the distal end part 12*d* of the endoscope 12.

The distal end part 12*d* of the endoscope 12 is provided with an illumination optical system 30*a* and an image pickup optical system 30*b*. The illumination optical system 30*a* includes an illumination lens 32, and the object to be observed is irradiated with illumination light, which is transmitted by the light guide 25, through the illumination lens 32. The image pickup optical system 30*b* includes an objective lens 42, a zoom lens 43, and an image pickup sensor 44. Light, which is emitted from the object to be observed since the object to be observed is irradiated with illumination light, is incident on the image pickup sensor 44 through the objective lens 42 and the zoom lens 43. Accordingly, the image of the object to be observed is formed on the image pickup sensor 44. The zoom lens 43 is a lens that is used to enlarge the object to be observed, and is moved between a telephoto end and a wide end in a case where the zoom operation part 12*h* is operated. Digital enlargement in which a part of an image obtained from the image pickup of the object to be observed is cut out and enlarged may be used as the enlargement of the object to be observed in addition to the optical enlargement of the object to be observed that is performed using the zoom lens 43.

Figure 6:
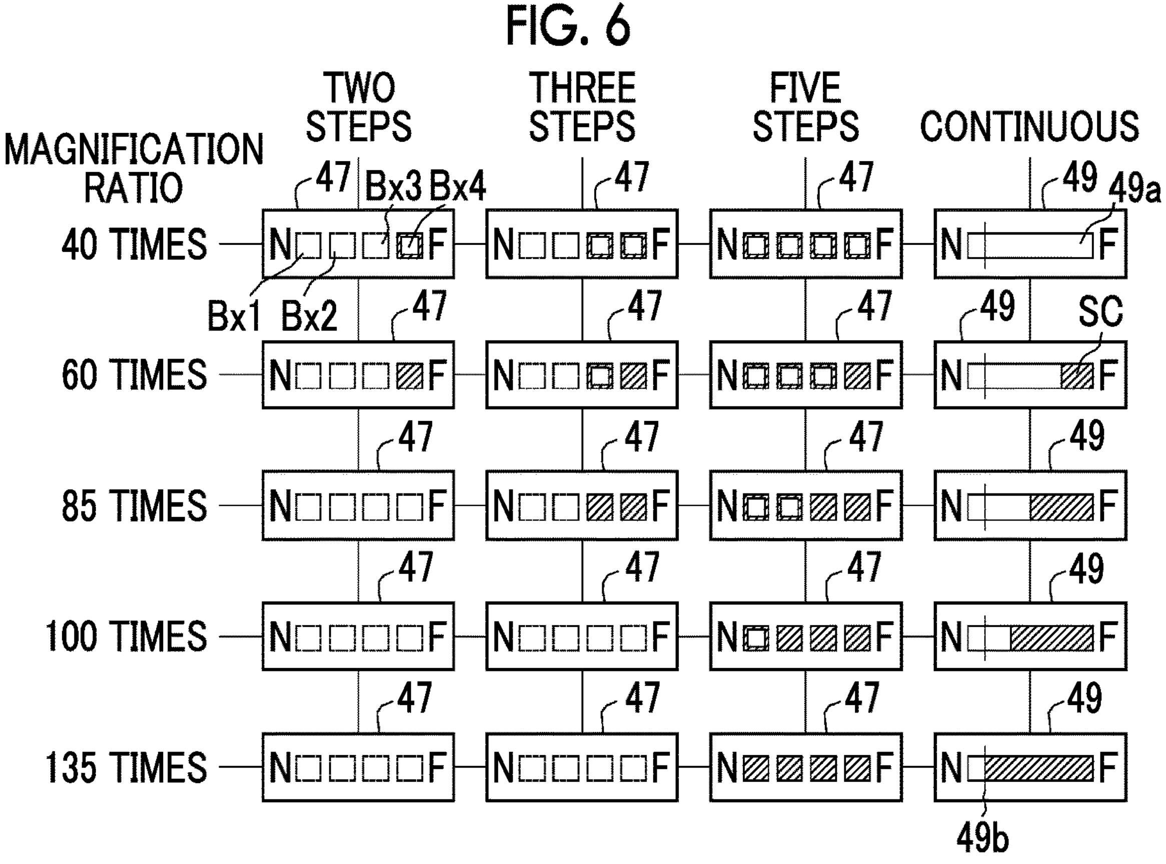
FIG. 6 is a diagram showing magnification ratio display sections that are displayed in a case where a magnification ratio is changed stepwise and magnification ratio display sections that are displayed in a case where a magnification ratio is continuously changed.

In this embodiment, the zoom lens 43 can be used to change a magnification ratio stepwise. Here, a magnification ratio is a value that is obtained in a case where the dimensions of an object displayed on the display 18 are divided by the actual dimensions of the object. For example, in a case where the display 18 is a 19-inch display, as shown in FIG. 6, a magnification ratio can be changed stepwise in two steps, three steps, and five steps, or a magnification ratio can be changed continuously. In order to display a magnification ratio, which is in use, on the display 18, a magnification ratio display section 47 that is displayed in a case where a magnification ratio is changed stepwise and a magnification ratio display section 49 that is displayed in a case where a magnification ratio is changed continuously are provided at a specific display position on the display 18. Any one of the magnification ratio display section 47 or the magnification ratio display section 49 is displayed on the actual display 18.

A magnification ratio in use is displayed in the magnification ratio display section 47 by combinations of the non-display of frame, the display of frame, and overall display of boxes Bx1, Bx2, Bx3, and Bx4 provided between N (Near) representing a near view and F (Far) representing a distant view. The size of the display 18 generally used in the endoscope system 10 is in the range of 19 to 32 inches, and the width of the display 18 is in the range of 23.65 cm to 39.83 cm.

Specifically, in a case where a two-step change in a magnification ratio for changing a magnification ratio to 40 times and 60 times is set, the frames of the boxes Bx1, Bx2, and Bx3 are not displayed. In a case where a magnification ratio in use is 40 times, the frame of the box Bx4 is displayed. In a case where a magnification ratio in use is 60 times, the box Bx4 is displayed overall. Further, in a case where a three-step change in a magnification ratio for changing a magnification ratio to 40 times, 60 times, and 85 times is set, the frames of the boxes Bx1 and Bx2 are not displayed. In a case where a magnification ratio in use is 40 times, the frames of the boxes Bx3 and Bx4 are displayed. Furthermore, in a case where a magnification ratio in use is 60 times, the frame of the box Bx3 is displayed and the box Bx4 is displayed overall. In a case where a magnification ratio in use is 85 times, the boxes Bx3 and Bx4 are displayed overall.

Moreover, in a case where a five-step change in a magnification ratio for changing a magnification ratio to 40 times, 60 times, 85 times, 100 times, and 135 times is set and a magnification ratio in use is 40 times, the frames of the boxes Bx1, Bx2, Bx3, and Bx4 are displayed. Further, in a case where a magnification ratio in use is 60 times, the frames of the boxes Bx1, Bx2, and Bx3 are displayed and the box Bx4 is displayed overall. Furthermore, in a case where a magnification ratio is 85 times, the frames of the boxes Bx1 and Bx2 are displayed and the boxes Bx3 and Bx4 are displayed overall. Further, in a case where a magnification ratio is 100 times, the frame of the box Bx1 is displayed and the boxes Bx2, Bx3, and Bx4 are displayed overall. Furthermore, in a case where a magnification ratio is 135 times, the frames of the boxes Bx1, Bx2, Bx3, and Bx4 are displayed overall.

The magnification ratio display section 49 comprises a horizontally long bar 49*a* that is provided between N (Near) representing a near view and F (Far) representing a distant view. In a case where a magnification ratio is in a range up to 40 times, only the frame of the horizontally long bar 49*a* is displayed. Further, in a case where a magnification ratio exceeds 40 times, the inside of the frame of the horizontally long bar 49*a* is displayed with a specific color SC. Further, until a magnification ratio reaches 135 times, the region having the specific color in the horizontally long bar 49*a* gradually expands to F side whenever a magnification ratio is increased. Then, in a case where a magnification ratio reaches 135 times, the region having the specific color expands up to an upper limit display bar 49*b* and does not expand to the F side any more.

As shown in FIG. 2, a charge coupled device (CCD) image pickup sensor or a complementary metal-oxide semiconductor (CMOS) image pickup sensor can be used as the image pickup sensor 44. Further, a complementary color image pickup sensor, which comprises complementary color filters corresponding to C (cyan), M (magenta), Y (yellow), and G (green), may be used instead of the primary color image pickup sensor 44. In a case where a complementary color image pickup sensor is used, image signals corresponding to four colors of C, M, Y, and G are output. Accordingly, the image signals corresponding to four colors of C, M, Y, and G are converted into image signals corresponding to three colors of R, G, and B by complementary color-primary color conversion, so that image signals corresponding to the same respective colors of R, G, and B as those of the image pickup sensor 44 can be obtained.

The image pickup sensor 44 is driven and controlled by the image pickup controller 45. A control performed by the image pickup controller 45 varies depending on the respective modes. In the normal light mode, the image pickup controller 45 controls the image pickup sensor 44 so that the image pickup sensor 44 picks up the image of the object to be observed illuminated with normal light. Accordingly, Bc-image signals are output from B-pixels of the image pickup sensor 44, Gc-image signals are output from G-pixels thereof, and Rc-image signals are output from R-pixels thereof.

In the special light mode, the image pickup controller 45 controls the image pickup sensor 44 so that the image pickup sensor 44 picks up the image of the object to be observed illuminated with special light. Accordingly, Bs-image signals are output from the B-pixels of the image pickup sensor 44, Gs-image signals are output from the G-pixels thereof, and Rs-image signals are output from the R-pixels thereof. In the disease-related processing mode, Bc-image signals, Gc-image signals, and Rc-image signals are output from the B-pixels, the G-pixels, and the R-pixels of the image pickup sensor 44 by illumination using special light even in any one of the first observation environment or the second observation environment.

A correlated double sampling/automatic gain control (CDS/AGC) circuit 46 performs correlated double sampling (CDS) or automatic gain control (AGC) on analog image signals that are obtained from the image pickup sensor 44. The image signals, which have been transmitted through the CDS/AGC circuit 46, are converted into digital image signals by an analog/digital (A/D) converter 48. The digital image signals, which have been subjected to A/D conversion, are input to the processor device 16.

In the processor device 16, programs related to various types of processing are incorporated into a program memory (not shown). The processor device 16 is provided with a central controller (not shown) that is formed of a processor. The programs incorporated into the program memory are executed by the central controller, so that the functions of an image acquisition unit 50, a digital signal processor (DSP) 52, a noise-reduction unit 54, an image processing unit 58, and a video signal generation unit 60 are realized.

The image acquisition unit 50 acquires the image signals of an endoscopic image that is one of medical images input from the endoscope 12. The acquired image signals are transmitted to the DSP 52. The DSP 52 performs various types of signal processing, such as defect correction processing, offset processing, gain correction processing, matrix processing, gamma conversion processing, demosaicing processing, and YC conversion processing, on the received image signals. Signals of defective pixels of the image pickup sensor 44 are corrected in the defect correction processing. Dark current components are removed from the image signals subjected to the defect correction processing in the offset processing, so that an accurate zero level is set. The image signals, which have been subjected to the offset processing and correspond to each color, are multiplied by a specific gain in the gain correction processing, so that the signal level of each image signal is adjusted. The matrix processing for improving color reproducibility is performed on the image signals that have been subjected to the gain correction processing and correspond to each color.

After that, the brightness or chroma saturation of each image signal is adjusted by the gamma conversion processing. The demosaicing processing (also referred to as equalization processing or demosaicing) is performed on the image signals subjected to the matrix processing, so that signals corresponding to colors missed in the respective pixels are generated by interpolation. All the pixels are made to have the signals corresponding to the respective colors of R, G, and B by the demosaicing processing. The DSP 52 performs the YC conversion processing on the respective image signals subjected to the demosaicing processing, and outputs luminance signals Y, color difference signals Cb, and color difference signals Cr to the noise-reduction unit 54. The noise-reduction unit 54 performs noise reduction processing, which is performed using, for example, a moving-average method, a median filtering method, or the like, on the image signals that have been subjected to the demosaicing processing and the like by the DSP 56.

The image processing unit 58 comprises a normal light image generation unit 62, a special light image generation unit 64, and a disease-related processing unit 66. The special light image generation unit 64 includes a color difference-expanded image generation unit 64*a*. The image processing unit 58 inputs Rc-image signals, Gc-image signals, and Bc-image signals to the normal light image generation unit 62 in the case of a normal light observation mode. Further, the image processing unit 58 inputs Rs-image signals, Gs-image signals, and Bs-image signals to the special light image generation unit 64 in the case of a special light observation mode or the disease-related processing mode. Furthermore, the image processing unit 58 inputs a special light image or a color difference-expanded image, which is generated by the special light image generation unit 64, to the disease-related processing unit 66 in the case of the disease-related processing mode.

The normal light image generation unit 62 performs image processing for a normal light image on the Rc-image signals, the Gc-image signals, and the Bc-image signals that are input and correspond to one frame. The image processing for a normal light image includes color conversion processing, such as 3×3-matrix processing, gradation transformation processing, and three-dimensional look up table (LUT) processing, and structure enhancement processing, such as color enhancement processing and spatial frequency emphasis. The Rc-image signals, the Gc-image signals, and the Bc-image signals subjected to the image processing for a normal light image are input to the video signal generation unit 60 as a normal light image.

The special light image generation unit 64 includes a processing unit in a case where color difference expansion processing is performed and a processing unit in a case where the color difference expansion processing is not performed. In a case where the color difference expansion processing is not performed, the special light image generation unit 64 performs image processing for a special light image on the Rs-image signals, the Gs-image signals, and the Bs-image signals that are input and correspond to one frame. The image processing for a special light image includes color conversion processing, such as 3×3-matrix processing, gradation transformation processing, and three-dimensional look up table (LUT) processing, and structure enhancement processing, such as color enhancement processing and spatial frequency emphasis. The Rs-image signals, the Gs-image signals, and the Bs-image signals subjected to the image processing for a special light image are input to the video signal generation unit 60 or the disease-related processing unit 66 as a special light image.

On the other hand, in a case where the color difference expansion processing is performed, the color difference-expanded image generation unit 64*a* performs the color difference expansion processing for expanding a color difference in a plurality of ranges to be observed on the Rs-image signals, the Gs-image signals, and the Bs-image signals, which are input and correspond to one frame, to generate a color difference-expanded image. The generated color difference-expanded image is input to the video signal generation unit 60 or the disease-related processing unit 66. The details of the color difference-expanded image generation unit 64*a* will be described later.

The disease-related processing unit 66 determines whether or not to switch the first observation environment to the second observation environment different from the first observation environment on the basis of a first medical image that is obtained from the image pickup of the object to be observed in the first observation environment, and performs disease state processing related to the state of a disease on the basis of a second medical image that is obtained from the image pickup of the object to be observed in the second observation environment. The disease state processing includes at least one of calculating an index value related to the stage of ulcerative colitis, determining the stage of ulcerative colitis, or determining whether or not ulcerative colitis has pathologically remitted on the basis of the special light image. Information about the determination result of whether or not ulcerative colitis has pathologically remitted is input to the video signal generation unit 60. The details of the disease-related processing unit 66 will be described later. A case where the disease-related processing unit 66 determines whether or not ulcerative colitis has pathologically remitted will be described in the first to third embodiments.

The video signal generation unit 60 converts the normal light image, the special light image, the color difference-expanded image, or the information about the determination result, which is output from the image processing unit 58, into video signals that allows the image or the information to be displayed on the display 18 in full color. The converted video signals are input to the display 18. Accordingly, the normal light image, the special light image, the color difference-expanded image, or the information about the determination result is displayed on the display 18.

Figure 7:
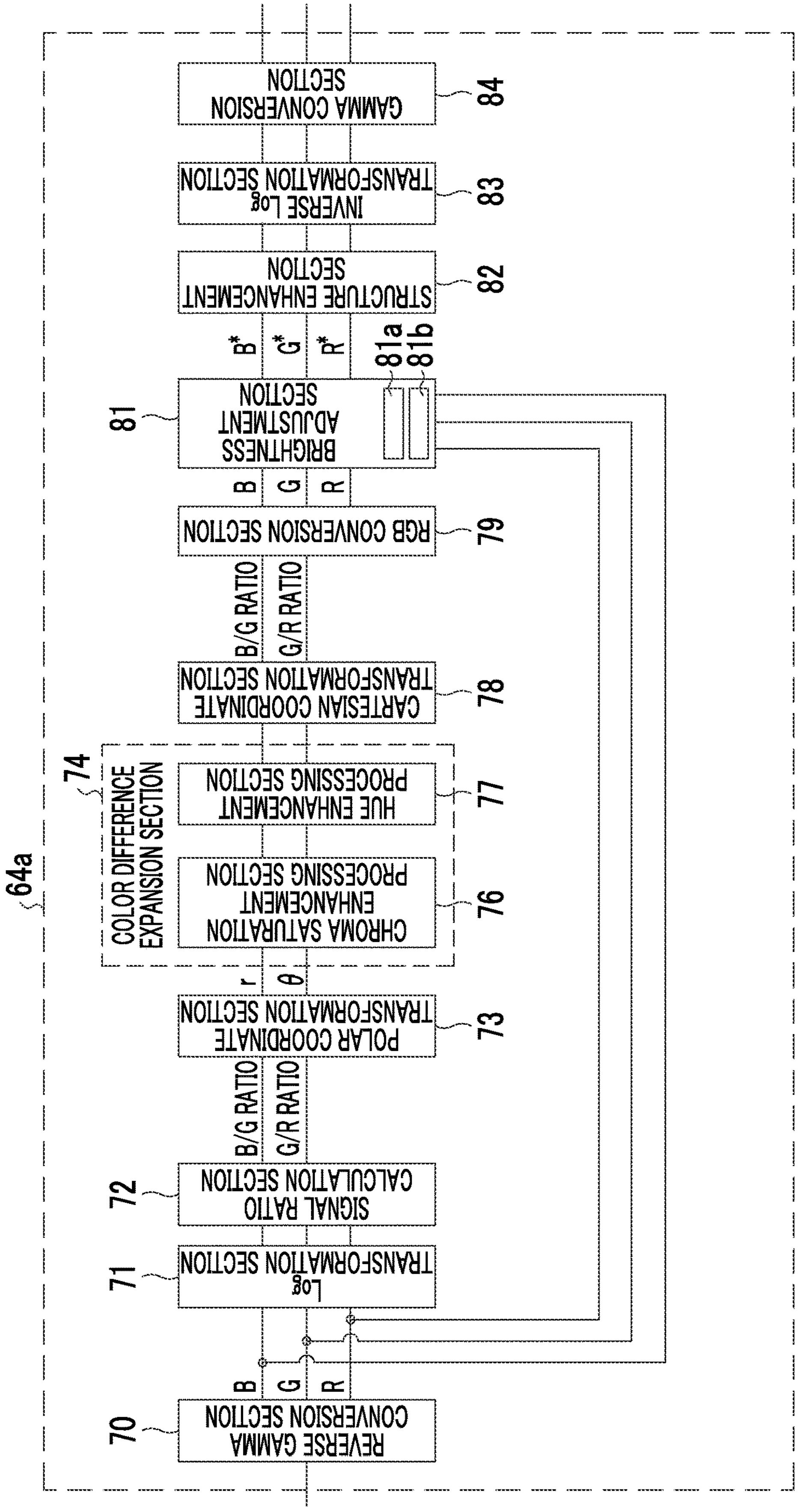
FIG. 7 is a block diagram showing the functions of a color difference-expanded image generation unit.

As shown in FIG. 7, the color difference-expanded image generation unit 64*a* comprises a reverse gamma conversion section 70, a Log transformation section 71, a signal ratio calculation section 72, a polar coordinate transformation section 73, a color difference expansion section 74, a Cartesian coordinate transformation section 78, an RGB conversion section 79, a brightness adjustment section 81, a structure enhancement section 82, an inverse Log transformation section 83, and a gamma conversion section 84.

Rs-image signals, Gs-image signals, and Bs-image signals based on special light are input to the reverse gamma conversion section 70. The reverse gamma conversion section 70 performs reverse gamma conversion on the input RGB three-channel digital image signals. Since the RGB image signals subjected to this reverse gamma conversion are linear reflectance-RGB signals that are linear in a reflectance from a sample, a ratio of signals related to a variety of biological information of the sample among the RGB image signals is high. A linear reflectance-R-image signal is referred to as a first R-image signal, a linear reflectance-G-image signal is referred to as a first G-image signal, and a linear reflectance-B-image signal is referred to as a first B-image signal. The first R-image signal, the first G-image signal, and the first B-image signal are collectively referred to as first RGB image signals.

The Log transformation section 71 performs Log transformation on each of the linear reflectance-RGB image signals. Accordingly, an R-image signal (log R) subjected to Log transformation, a G-image signal (log G) subjected to Log transformation, and a B-image signal (log B) subjected to Log transformation are obtained. The signal ratio calculation section 72 (corresponding to "color information acquisition section" of the present invention) calculates a B/G ratio (a value obtained after "−log" is omitted from −log(B/G) is written as "BIG ratio") by performing differential processing (log G−log B=log G/B=−log(B/G)) on the basis of the G-image signal and the B-image signal subjected to Log transformation. Further, the signal ratio calculation section 72 calculates a G/R ratio by performing differential processing (log R−log G=log R/G=−log(G/R)) on the basis of the R-image signal and the G-image signal subjected to Log transformation. Like the B/G ratio, a value obtained after "−log" is omitted from −log(G/R) is referred to as "G/R ratio".

The B/G ratio and the G/R ratio are obtained for each pixel from the pixel values of pixels that are present at the same positions in the B-image signals, the G-image signals, and the R-image signals. Further, the B/G ratio and the G/R ratio are obtained for each pixel. Furthermore, the B/G ratio correlates with a blood vessel depth (a distance between the surface of a mucous membrane and the position of a specific blood vessel). Accordingly, in a case where a blood vessel depth varies, the B/G ratio is also changed with a variation in blood vessel depth. Moreover, the G/R ratio correlates with the amount of blood (hemoglobin index). Accordingly, in a case where the amount of blood is changed, the G/R ratio is also changed with a variation in the amount of blood.

The polar coordinate transformation section 73 transforms the B/G ratio and the G/R ratio, which are obtained from the signal ratio calculation section 72, into a radius vector r and an angle θ. In the polar coordinate transformation section 73, the transformation of the B/G ratio and the G/R ratio into the radius vector r and the angle θ are performed for all the pixels. The color difference expansion section 74 performs color difference expansion processing for expanding a color difference between a normal mucous membrane and an abnormal region, such as a lesion area including ulcerative colitis, of a plurality of ranges to be observed in a signal ratio space (feature space) formed by the B/G ratio and the G/R ratio that are one of a plurality of pieces of color information. The expansion of a chroma saturation difference between the normal mucous membrane and the abnormal region or the expansion of a hue difference between the normal mucous membrane and the abnormal region is performed in this embodiment as the color difference expansion processing. For this purpose, the color difference expansion section 74 includes a chroma saturation enhancement processing section 76 and a hue enhancement processing section 77.

The chroma saturation enhancement processing section 76 performs chroma saturation enhancement processing for expanding a chroma saturation difference between the normal mucous membrane and the abnormal region in the signal ratio space. Specifically, the chroma saturation enhancement processing is performed by the expansion or compression of the radius vector r in the signal ratio space. The hue enhancement processing section 77 performs hue enhancement processing for expanding a hue difference between the normal mucous membrane and the abnormal region in the signal ratio space. Specifically, the hue enhancement processing is performed by the expansion or compression of the angle θ in the signal ratio space. The details of the chroma saturation enhancement processing section 76 and the hue enhancement processing section 77 having been described above will be described later.

The Cartesian coordinate transformation section 78 transforms the radius vector r and the angle θ, which have been subjected to the chroma saturation enhancement processing and the hue enhancement processing, into Cartesian coordinates. Accordingly, the radius vector r and the angle θ are transformed into the B/G ratio and the G/R ratio subjected to the expansion/compression of the angle. The RGB conversion section 79 converts the B/G ratio and the G/R ratio, which have been subjected to the chroma saturation enhancement processing and the hue enhancement processing, into second RGB image signals using at least one image signal of the first RGB image signals. For example, the RGB conversion section 79 converts the B/G ratio into a second B-image signal by performing an arithmetic operation that is based on the first G-image signal of the first RGB image signals and the B/G ratio. Further, the RGB conversion section 79 converts the G/R ratio into a second R-image signal by performing an arithmetic operation that is based on the first G-image signal of the first RGB image signals and the G/R ratio. Furthermore, the RGB conversion section 79 outputs the first G-image signal as a second G-image signal without performing special conversion. The second R-image signal, the second G-image signal, and the second B-image signal are collectively referred to as the second RGB image signals.

The brightness adjustment section 81 adjusts the pixel values of the second RGB image signals using the first RGB image signals and the second RGB image signals. The reason why the brightness adjustment section 81 adjusts the pixel values of the second RGB image signals is as follows. The brightness of the second RGB image signals, which are obtained from processing for expanding or compressing a color region by the chroma saturation enhancement processing section 76 and the hue enhancement processing section 77, may be significantly different from that of the first RGB image signals. Accordingly, the pixel values of the second RGB image signals are adjusted by the brightness adjustment section 81 so that the second RGB image signals subjected to brightness adjustment have the same brightness as the first RGB image signals.

The brightness adjustment section 81 comprises a first brightness information-calculation section 81*a* that obtains first brightness information Yin on the basis of the first RGB image signals, and a second brightness information-calculation section 81*b* that obtains second brightness information Yout on the basis of the second RGB image signals. The first brightness information-calculation section 81*a* calculates the first brightness information Yin according to an arithmetic expression of "kr×pixel value of first R-image signal+kg×pixel value of first G-image signal+kb×pixel value of first B-image signal". Like the first brightness information-calculation section 81*a*, the second brightness information-calculation section 81*b* also calculates the second brightness information Yout according to the same arithmetic expression as described above. In a case where the first brightness information Yin and the second brightness information Yout are obtained, the brightness adjustment section 81 adjusts the pixel values of the second RGB image signals by performing arithmetic operations that are based on the following equations (E1) to (E3).

$$R^{*}=\text{pixel value of second } R\text{-image signal}\times Yin/Yout \quad \text{(E1):}$$

$$G^{*}=\text{pixel value of second } G\text{-image signal}\times Yin/Yout \quad \text{(E2):}$$

$$B^{*}=\text{pixel value of second } B\text{-image signal}\times Yin/Yout \quad \text{(E3):}$$

"R*" denotes the second R-image signal subjected to brightness adjustment, "G*" denotes the second G-image signal subjected to brightness adjustment, and "B*" denotes the second B-image signal subjected to brightness adjustment. Further, "kr", "kg", and "kb" are arbitrary constants that are in the range of "0" to "1".

The structure enhancement section 82 performs structure enhancement processing on the second RGB image signals having passed through the RGB conversion section 79. Frequency filtering or the like is used as the structure enhancement processing. The inverse Log transformation section 83 performs inverse Log transformation on the second RGB image signals having passed through the structure enhancement section 82. Accordingly, second RGB image signals having anti-logarithmic pixel values are obtained. The gamma conversion section 84 performs gamma conversion on the RGB image signals having passed through the inverse Log transformation section 83. Accordingly, second RGB image signals having gradations suitable for an output device, such as the display 18, are obtained. The second RGB image signals having passed through the gamma conversion section 84 are transmitted to the video signal generation unit 60.

Figure 8:
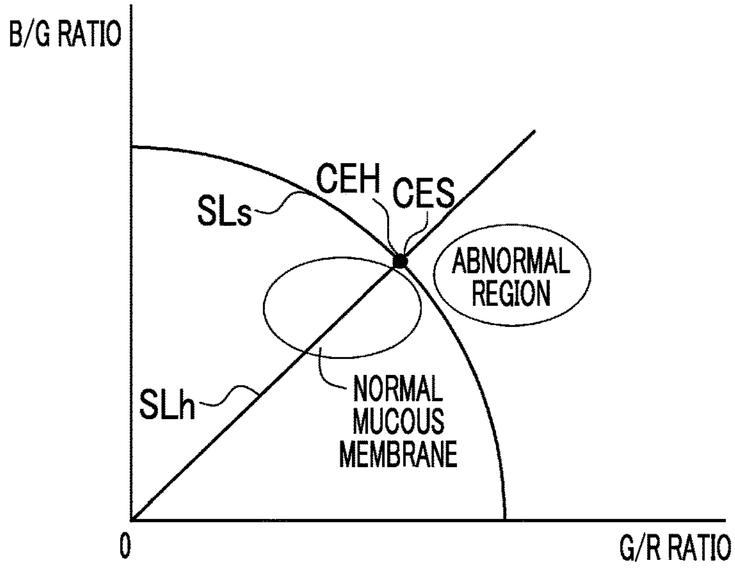
FIG. 8 is a diagram illustrating a normal mucous membrane and an abnormal region in a signal ratio space.

The chroma saturation enhancement processing section 76 and the hue enhancement processing section 77 increase a chroma saturation difference or a hue difference between a normal mucous membrane and an abnormal region that are distributed in a first quadrant of the signal ratio space (feature space) formed by the B/G ratio and the G/R ratio as shown in FIG. 8. The abnormal region is distributed at various positions other than the normal mucous membrane in the signal ratio space, but is assumed as a reddish lesion area in this embodiment. The color difference expansion section 74 determines an expansion center in the signal ratio space so that a color difference between the normal mucous membrane and the abnormal region expands. Specifically, the chroma saturation enhancement processing section 76 determines an expansion center CES and an expansion center line SLs for chroma saturation that are used to expand a chroma saturation difference between the normal mucous membrane and the abnormal region. Further, the hue enhancement processing section 77 determines an expansion center CEH and an expansion center line SLh for hue that are used to expand a hue difference between the normal mucous membrane and the abnormal region.

Figure 9:
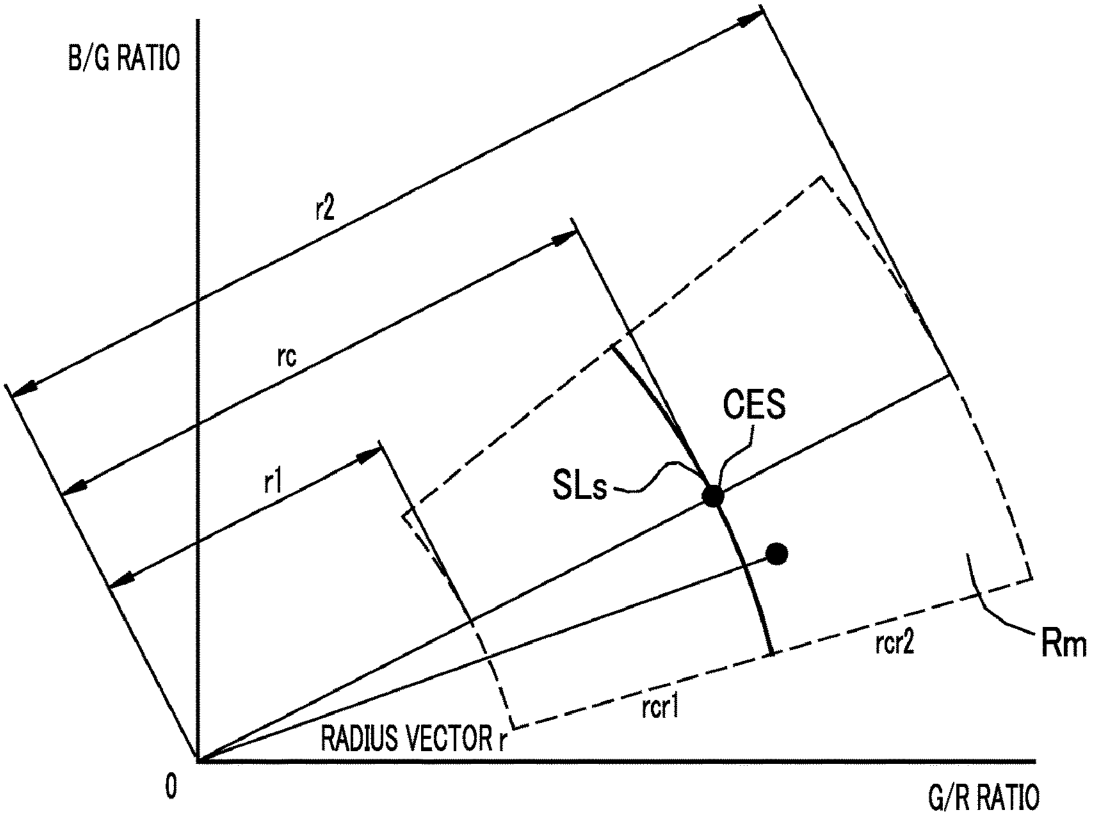
FIG. 9 is a diagram illustrating a radius vector change range Rm.

As shown in FIG. 9, the chroma saturation enhancement processing section 76 changes a radius vector r, which is represented by coordinates positioned inside a radius vector change range Rm, in the signal ratio space but does not change a radius vector r that is represented by coordinates positioned outside the radius vector change range Rm. In the radius vector change range Rm, the radius vector r is in the range of "r1" to "r2" (r1<r<r2). Further, an expansion center line SLs for chroma saturation is set on a radius vector rc positioned between the radius vector r1 and the radius vector r2 in the radius vector change range Rm.

Here, as the radius vector r is larger, chroma saturation is higher. Accordingly, a range rcr1 (r1<r<rc) in which the radius vector r is smaller than the radius vector rc represented by the expansion center line SLs for chroma saturation is defined as a low chroma saturation range. On the other hand, a range rcr2 (rc<r<r2) in which the radius vector r is larger than the radius vector rc represented by the expansion center line SLs for chroma saturation is defined as a high chroma saturation range.

Figure 10:
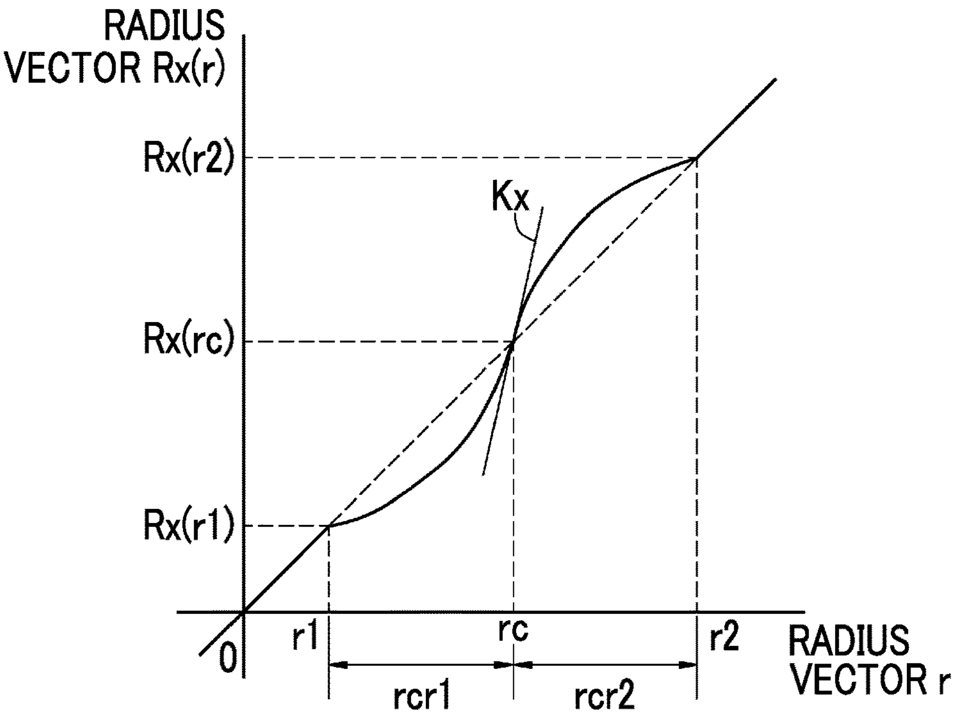
FIG. 10 is a graph showing a relationship between a radius vector r and a radius vector Rx(r) that is obtained after chroma saturation enhancement processing.

As shown in FIG. 10, the chroma saturation enhancement processing outputs a radius vector Rx(r) in response to the input of the radius vector r of coordinates included in the radius vector change range Rm. A relationship between the input and output of the chroma saturation enhancement processing is shown by a solid line. In the chroma saturation enhancement processing, an S-shaped conversion curve is used and an output value Rx(r) is made smaller than an input value r in a low chroma saturation range rcr1 but an output value Rx(r) is made larger than an input value r in a high chroma saturation range rcr2. Further, an inclination Kx of Rx(rc) is set to "1" or more. Accordingly, the chroma saturation of an object to be observed included in the low chroma saturation range can be made lower, but the chroma saturation of an object to be observed included in the high chroma saturation range can be made higher. A chroma saturation difference between a plurality of ranges to be observed can be increased by such chroma saturation enhancement processing.

Figure 11:
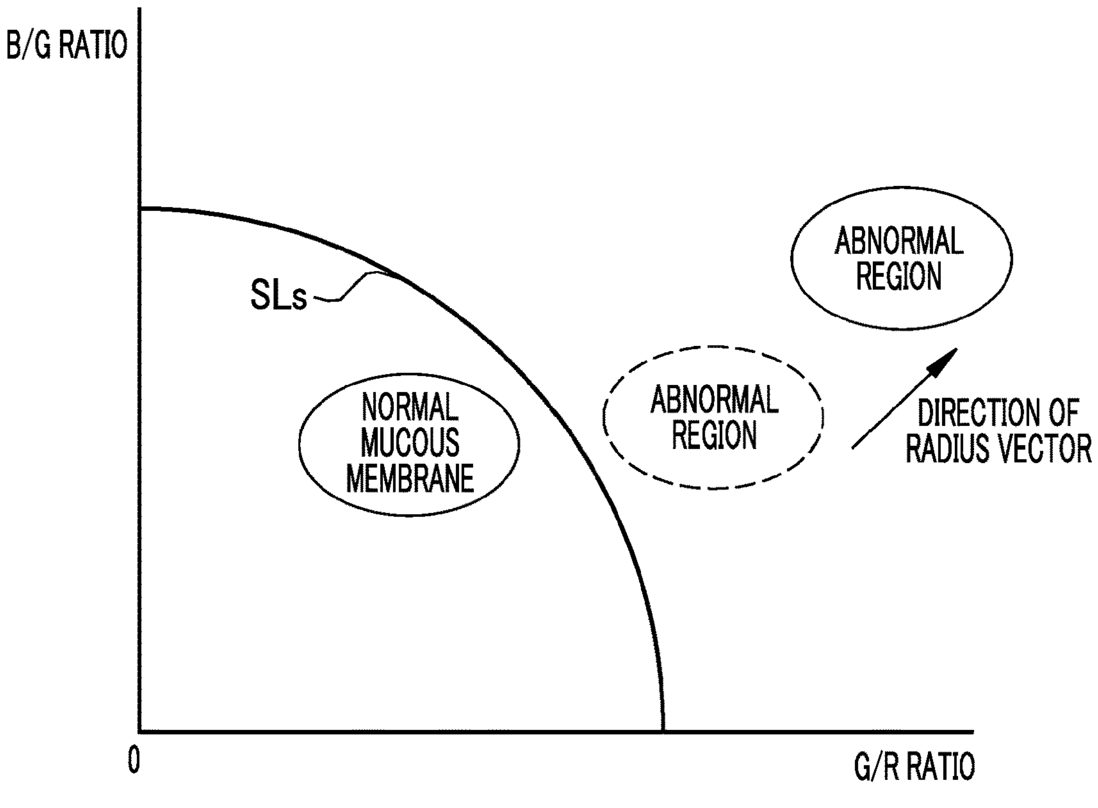
FIG. 11 is a diagram illustrating a positional relationship between abnormal regions before and after chroma saturation enhancement processing in the signal ratio space.

In a case where the chroma saturation enhancement processing is performed as described above, an abnormal region (solid line) subjected to the chroma saturation enhancement processing is moved to be farther from the expansion center line SLs for chroma saturation than an abnormal region (dotted line) not yet subjected to the chroma saturation enhancement processing as shown in FIG. 11. Since the direction of a radius vector in the feature space represents the magnitude of chroma saturation, a chroma saturation difference between the abnormal region (solid line) subjected to the chroma saturation enhancement processing and the normal mucous membrane is larger than a chroma saturation difference between the abnormal region (dotted line) not yet subjected to the chroma saturation enhancement processing and the normal mucous membrane.

Figure 12:
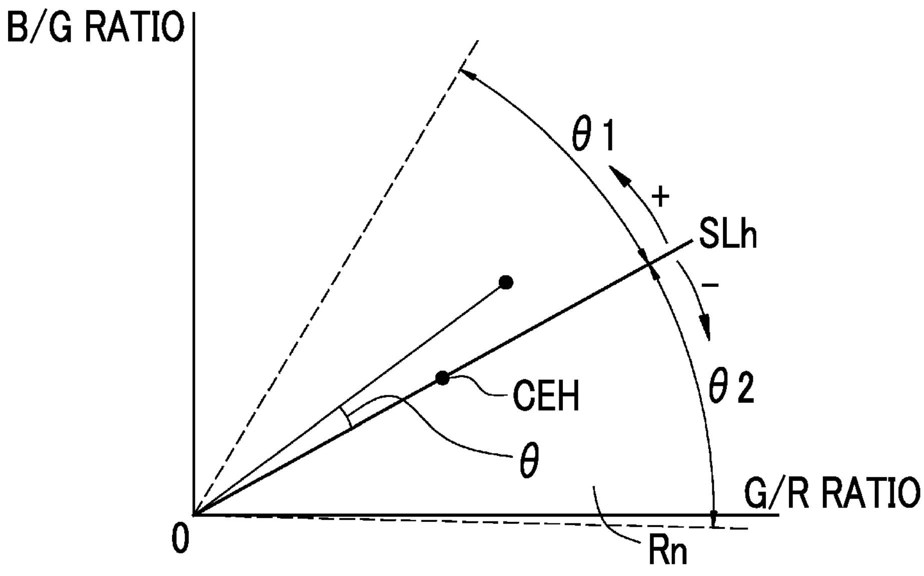
FIG. 12 is a diagram illustrating an angle change range Rn.

As shown in FIG. 12, the hue enhancement processing section 77 changes an angle θ, which is represented by coordinates positioned inside an angle change range Rn, in the signal ratio space but does not change an angle θ that is represented by coordinates positioned outside the angle change range Rn. The angle change range Rn is formed of the range of an angle θ1 in a counterclockwise direction (first hue direction) from an expansion center line SLh for hue and the range of an angle θ2 in a clockwise direction (second hue direction) from the expansion center line SLh for hue.

The angle θ of coordinates included in the angle change range Rn is redefined as an angle θ from the expansion center line SLh for hue, the side of the expansion center line SLh for hue θ corresponding to the counterclockwise direction is defined as a positive side, and the side of the expansion center line SLh for hue corresponding to the clockwise direction is defined as a negative side. In a case where the angle θ is changed, hue is also changed. Accordingly, the range of the angle θ1 of the angle change range Rn is defined as a positive hue range θ1, and the range of the angle θ2 thereof is defined as a negative hue range θ2. It is preferable that the expansion center line SLh for hue is also a line intersecting with the range of the normal mucous membrane in the feature space like the expansion center line SLs for chroma saturation.

Figure 13:
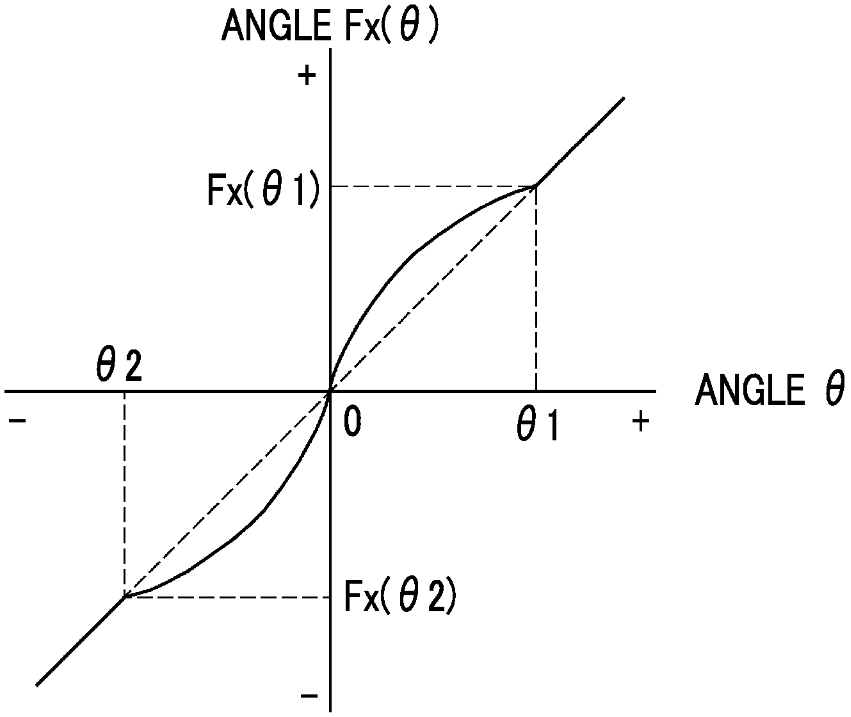
FIG. 13 is a graph showing a relationship between an angle θ and an angle Fx(θ) that is obtained after hue enhancement processing.

As shown in FIG. 13, the hue enhancement processing outputs an angle Fx(θ) in response to the input of the angle θ of coordinates included in the angle change range Rn. A relationship between the input and output of the hue enhancement processing is shown by a solid line. In the hue enhancement processing, an output Fx(θ) is made smaller than an input θ in the negative hue range θ2 but an output Fx(θ) is made larger than an input θ in the positive hue range θ1. Accordingly, a difference in hue between an object to be observed included in the negative hue range and an object to be observed included in the positive hue range can be increased.

Figure 14:
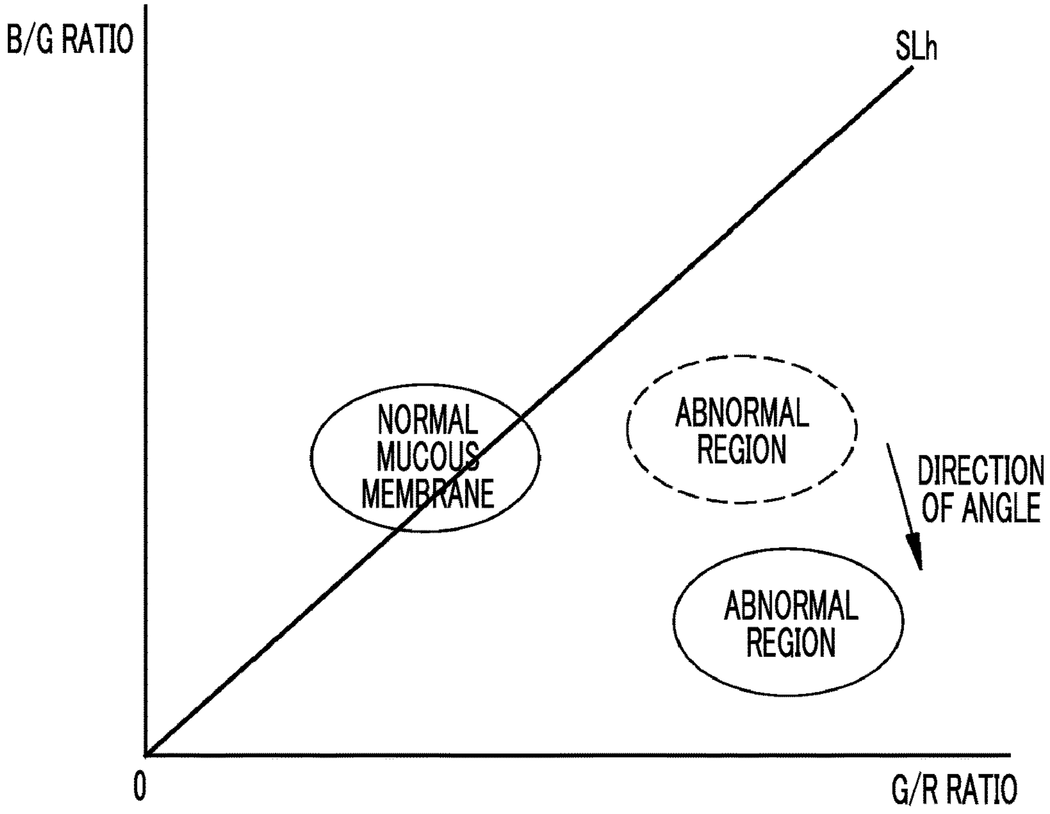
FIG. 14 is a diagram illustrating a positional relationship between abnormal regions before and after hue enhancement processing in the signal ratio space.

In a case where the hue enhancement processing is performed as described above, an abnormal region (solid line) subjected to the hue enhancement processing is moved to be farther from the expansion center line SLh for hue than an abnormal region (dotted line) not yet subjected to the hue enhancement processing as shown in FIG. 14. Since the direction of an angle in the feature space represents a difference in hue, a hue difference between the abnormal region (solid line) subjected to the hue enhancement processing and the normal mucous membrane is larger than a hue difference between the abnormal region (dotted line) not yet subjected to the hue enhancement processing and the normal mucous membrane.

The feature space may be an ab space that is formed by a* and b* (indicating the tint elements a* and b* of a CIE Lab space that are color information. The same applies hereinafter) obtained from the Lab conversion of the first RGB image signals that is performed by a Lab conversion unit, a Cr,Cb space that is formed by color difference signals Cr and Cb, or a HS space that is formed by hue H and chroma saturation S, in addition to the signal ratio space.

Figure 15:
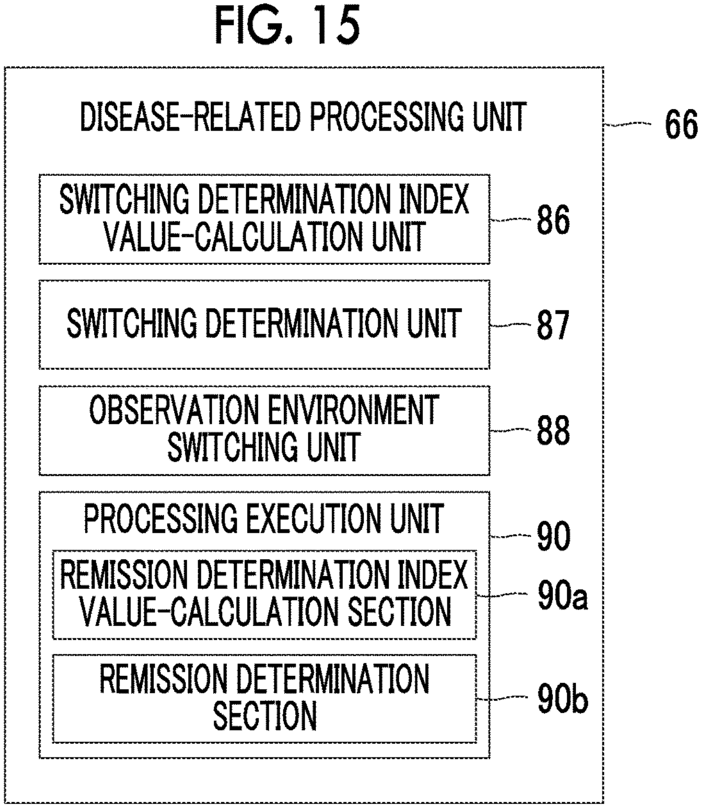
FIG. 15 is a block diagram showing the functions of a disease-related processing unit.

As shown in FIG. 15, the disease-related processing unit 66 comprises a switching determination index value-calculation unit 86, a switching determination unit 87, an observation environment switching unit 88, and a processing execution unit 90. The switching determination index value-calculation unit 86 calculates a switching determination index value, which is used to determine whether or not to switch the first observation environment to the second observation environment, on the basis of the first medical image. Here, in the first observation environment, the object to be observed is enlarged at the first magnification ratio and the object to be observed is illuminated with special light. Further, the first medical image is displayed on the display 18 in the first observation environment. It is preferable that the first medical image is the color difference-expanded image. In the second observation environment, the object to be observed is enlarged at the second magnification ratio and the object to be observed is illuminated with special light. Further, the second medical image is displayed on the display 18 in the second observation environment. It is preferable that the second medical image is the special light image.

Figure 16:
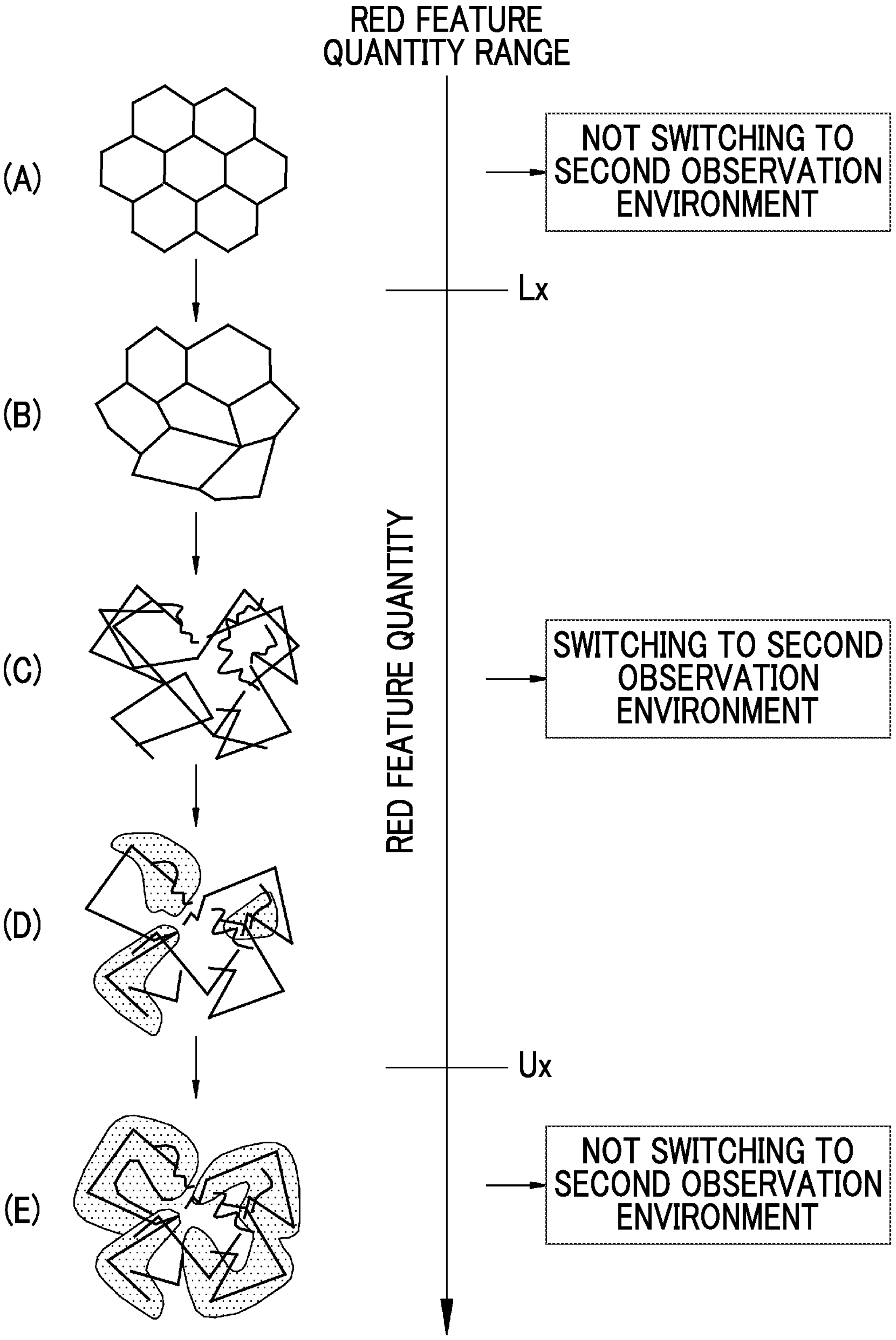
FIG. 16 is a diagram illustrating determination related to switching to a second observation environment.

It is preferable that the first magnification ratio is a magnification ratio allowing a user to visually determine whether or not ulcerative colitis has pathologically remitted without using the automatic determination of whether or not the disease has pathologically remitted performed by the remission determination section 90*b* for patterns in which it is clear whether or not ulcerative colitis has pathologically remitted (patterns of (A) and (E) of FIG. 16). On the other hand, it is preferable that the second magnification ratio is a magnification ratio enough to allowing the remission determination section 90*b* to accurately perform the automatic determination of whether or not a disease has pathologically remitted for patterns in which it is difficult for a user to visually determine whether or not ulcerative colitis has pathologically remitted (patterns of (B), (C), and (D) of FIG. 16). For example, it is preferable that the first magnification ratio is less than 60 times and the second magnification ratio is 60 times or more.

The switching determination index value-calculation unit 86 calculates a red feature quantity, which represents a red component caused by the rubor of the object to be observed, as a switching determination index value on the basis of a color difference-enhanced image that is the first medical image. It is preferable that the red feature quantity is the number of pixels of which a threshold value for red has a pixel value equal to or larger than a certain value in a red image of the color difference-enhanced image.

The switching determination unit 87 determines whether or not to switch the first observation environment to the second observation environment on the basis of the switching determination index value. Specifically, in a case where the red feature quantity is smaller than a lower limit Lx of a red feature quantity range (the colitis of the object to be observed is weak) or a case where the red feature quantity is equal to or larger than an upper limit Ux of the red feature quantity range (the colitis of the object to be observed is strong), the switching determination unit 87 determines that switching to the second observation environment is not to be performed as shown in (A) to (E) of FIG. 16 since the disease is in the state of the disease (patterns (A) and (E)) in which a user can visually determine whether or not the disease has pathologically remitted in the color difference-expanded image. On the other hand, in a case where the red feature quantity is in the red feature quantity range, the switching determination unit 87 determines that switching to the second observation environment is to be performed since the disease is in the state of the disease (patterns (B), (C), and (D)) in which it is difficult for a user to visually determine whether or not the disease has pathologically remitted in the color difference-expanded image. The disease-related processing unit 66 may automatically determine that the disease has pathologically remitted in a case where the red feature quantity is smaller than the lower limit Lx of the red feature quantity range, and may automatically determine that the disease has not pathologically remitted in a case where the red feature quantity is equal to or larger than the upper limit Ux of the red feature quantity range. It is preferable that a determination result in this case is displayed on the display 18.

The inventors have found that the pattern of vascular structure is changed as the state of ulcerative colitis, which is one of the states of diseases, whenever the severity of ulcerative colitis worsens. In a case where ulcerative colitis has pathologically remitted or ulcerative colitis does not occur (or a case where ulcerative colitis is endoscopically mild), the pattern of superficial blood vessels is regular as shown in (A) of FIG. 16 or the regularity of the pattern of superficial blood vessels is somewhat disturbed as shown in (B) of FIG. 16. On the other hand, in a case where ulcerative colitis has not pathologically remitted and is endoscopically mild, a pattern in which superficial blood vessels are locally dense is found ((C) of FIG. 16). Further, in a case where ulcerative colitis has not pathologically remitted and is endoscopically moderate, a pattern in which intramucosal hemorrhage occurs is found ((D) of FIG. 16). Furthermore, in a case where ulcerative colitis has not pathologically remitted and is endoscopically severe, a pattern in which extramucosal hemorrhage occurs is found ((E) of FIG. 16).

Figure 17:
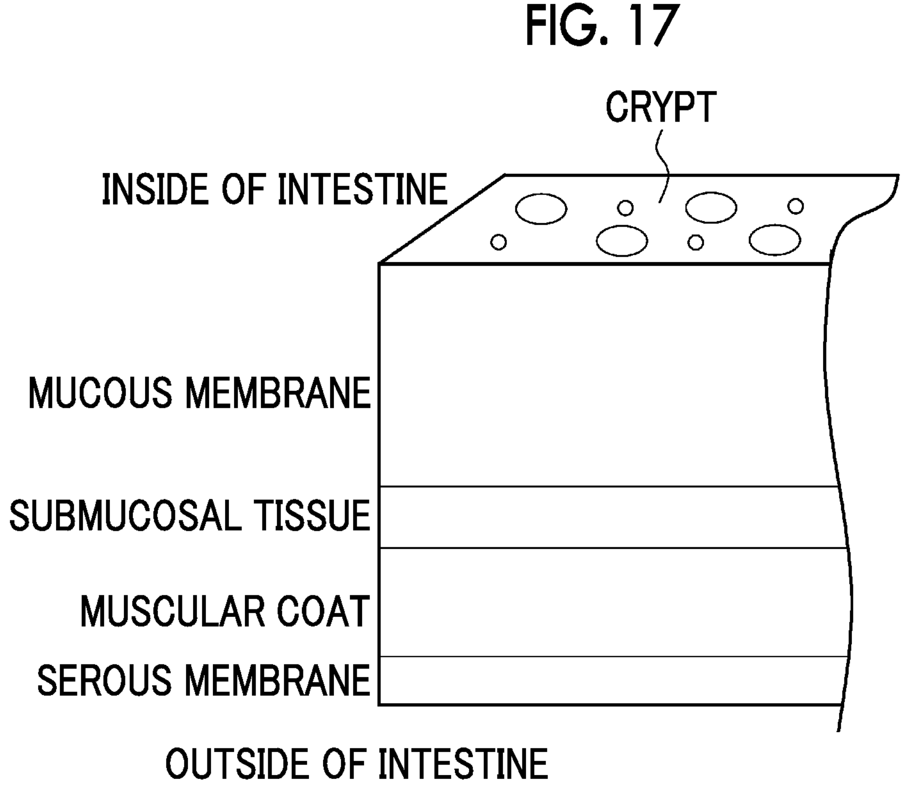
FIG. 17 is a cross-sectional view showing the cross section of a large intestine.

Here, "the denseness of superficial blood vessels" means a state where superficial blood vessels meander and are gathered, and means that some superficial blood vessels surround the crypt as shown in FIG. 17 in terms of appearance on an image. "Intramucosal hemorrhage" means bleeding in the mucosal tissue and requires to be discerned from bleeding into an inner cavity. "Intramucosal hemorrhage" means bleeding that is not in a mucous membrane and an inner cavity (the lumen and a hole having plicae) in terms of appearance on an image. "Extramucosal hemorrhage" means a small amount of blood that flows into the lumen, blood that is oozed from the lumen or the mucous membrane positioned in front of the endoscope even after the washing of the inside of the lumen and can be visually recognized, or blood in the lumen that is caused by bleeding on a hemorrhagic mucous membrane.

Figure 18:
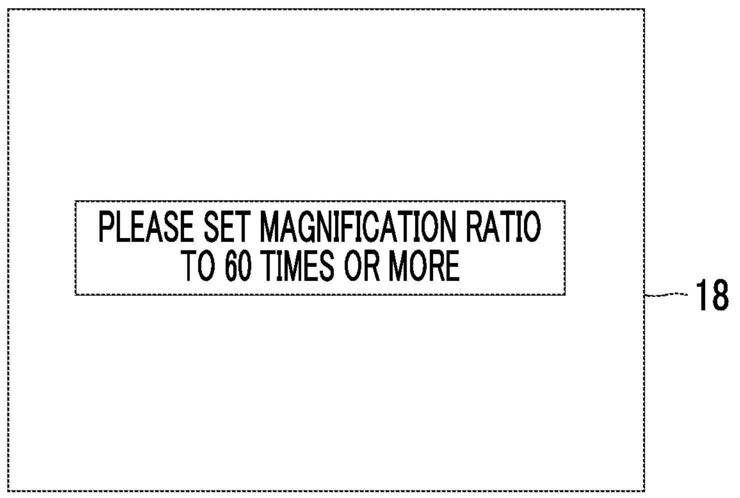
FIG. 18 is an image diagram showing a message that is notified in a case where it is determined that switching to the second observation environment is to be performed.

In a case where it is determined that switching to the second observation environment is to be performed, the observation environment switching unit 88 sets the magnification ratio of the object to be observed to the second magnification ratio by a specific operation and switches the first observation environment to the second observation environment. Specifically, the observation environment switching unit 88 sets the magnification ratio to the second magnification ratio by giving an instruction to automatically operate the zoom operation part 12*h* as the specific operation. Alternatively, the observation environment switching unit 88 displays a message (notification) of "Please set the magnification ratio to 60 times or more" on the display 18 as the specific operation as shown in FIG. 18. A user looks at the message displayed on the display 18 and operates the zoom operation part 12*h* to perform an operation for setting the magnification ratio to the second magnification ratio (60 times or more) as the specific operation. Further, the observation environment switching unit 88 switches an image, which is displayed on the display 18, to the special light image, which is not subjected to color difference enhancement processing, from the color difference-enhanced image. The special light image is used for the disease state processing in addition to the display on the display 18. The type and spectrum of illumination light may be switched in addition to the magnification ratio by the observation environment switching unit 88. For example, the special light may be switched to the normal light or the emission of four-color special light may be switched to the emission of violet light V having a single color.

The processing execution unit 90 performs the disease state processing, which is related to the state of a disease, on the basis of the second medical image. The processing execution unit 90 comprises a remission determination index value-calculation section 90*a* and a remission determination section 90*b*. The remission determination index value-calculation section 90*a* calculates a bleeding index value that represents the degree of bleeding of the object to be observed, or the degree of irregularity of superficial blood vessels. Specifically, it is preferable that a bleeding index value is the number of pixels having pixel values equal to or smaller than a threshold value for blue in a blue image of the special light image. The pixels having pixel values equal to or smaller than the threshold value for blue can be regarded as pixels of which the pixel values are reduced due to the light absorption of hemoglobin of superficial blood vessels. It is preferable that the degree of irregularity of superficial blood vessels is the number of pixels of a region in which the density of superficial blood vessels included in the special light image is equal to or higher than a threshold value for density. It is preferable that superficial blood vessels are extracted from the special light image through Laplacian processing and the density of superficial blood vessels is calculated on the basis of the extracted superficial blood vessels. Specifically, the density may be the density of superficial blood vessels in a specific region SA (=the number of superficial blood vessels/the number of pixels of a specific region SA). With regard to the bleeding index value or the density of superficial blood vessels, machine learning or the like is performed and the special light image is input to a machine-learned model, so that the model may output the bleeding index value or the density of superficial blood vessels.

Figure 19:
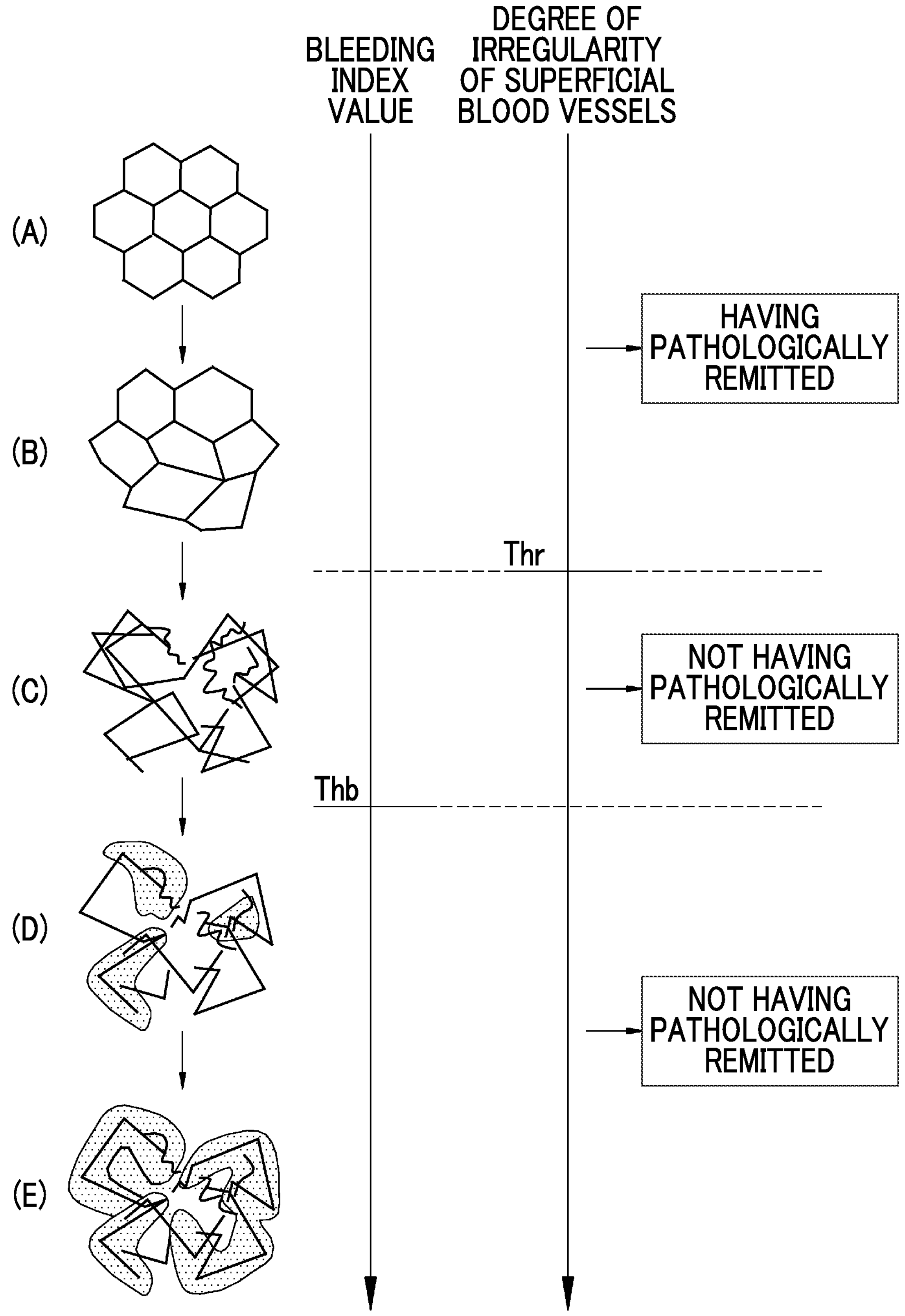
FIG. 19 is a diagram illustrating the determination of whether or not a disease has pathologically remitted based on a bleeding index value or the degree of irregularity of superficial blood vessels.
Figure 20:
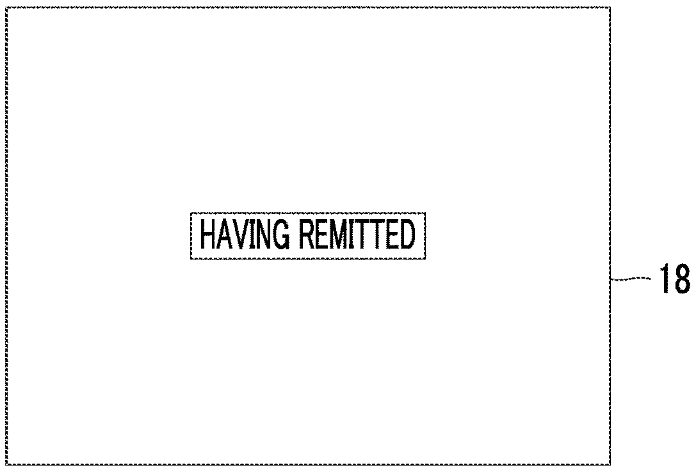
FIG. 20 is an image diagram showing a message that is notified in a case where it is determined that a disease is in pathological remission.

The remission determination section 90*b* determines whether or not a disease has pathologically remitted on the basis of the bleeding index value or the degree of irregularity of superficial blood vessels. Specifically, in a case where the bleeding index value is equal to or smaller than a threshold value Thb for bleeding and the degree of irregularity of superficial blood vessels is equal to or smaller than a threshold value Thr for the degree of irregularity, the remission determination section 90*b* determines that ulcerative colitis has pathologically remitted as shown in (A) to (E) of FIG. 19. On the other hand, in a case where any one of a condition in which the bleeding index value exceeds the threshold value Thb for bleeding or a condition in which the degree of irregularity of superficial blood vessels exceeds the threshold value Thr for the degree of irregularity is satisfied, the remission determination section 90*b* determines that ulcerative colitis has not pathologically remitted. In a case where determination processing performed by the remission determination section 90*b* is used, it is possible to determine the state of a disease (patterns (B), (C), and (D)), in which it is difficult for a user to visually determine whether or not a disease has pathologically remitted. In a case where it is determined that ulcerative colitis has pathologically remitted, it is preferable that a message that the ulcerative colitis has pathologically remitted is displayed on the display 18 as shown in FIG. 20. Although the remission determination section 90*b* can make a determination even in the first observation environment, the determination accuracy of the remission determination section 90*b* (see FIG. 15) in the second observation environment is higher than the determination accuracy of the remission determination section 90*b* in the first observation environment. Accordingly, it is preferable that the remission determination section 90*b* makes a determination in the second observation environment in a case where the remission determination section 90*b* is to make a determination.

Figure 21:
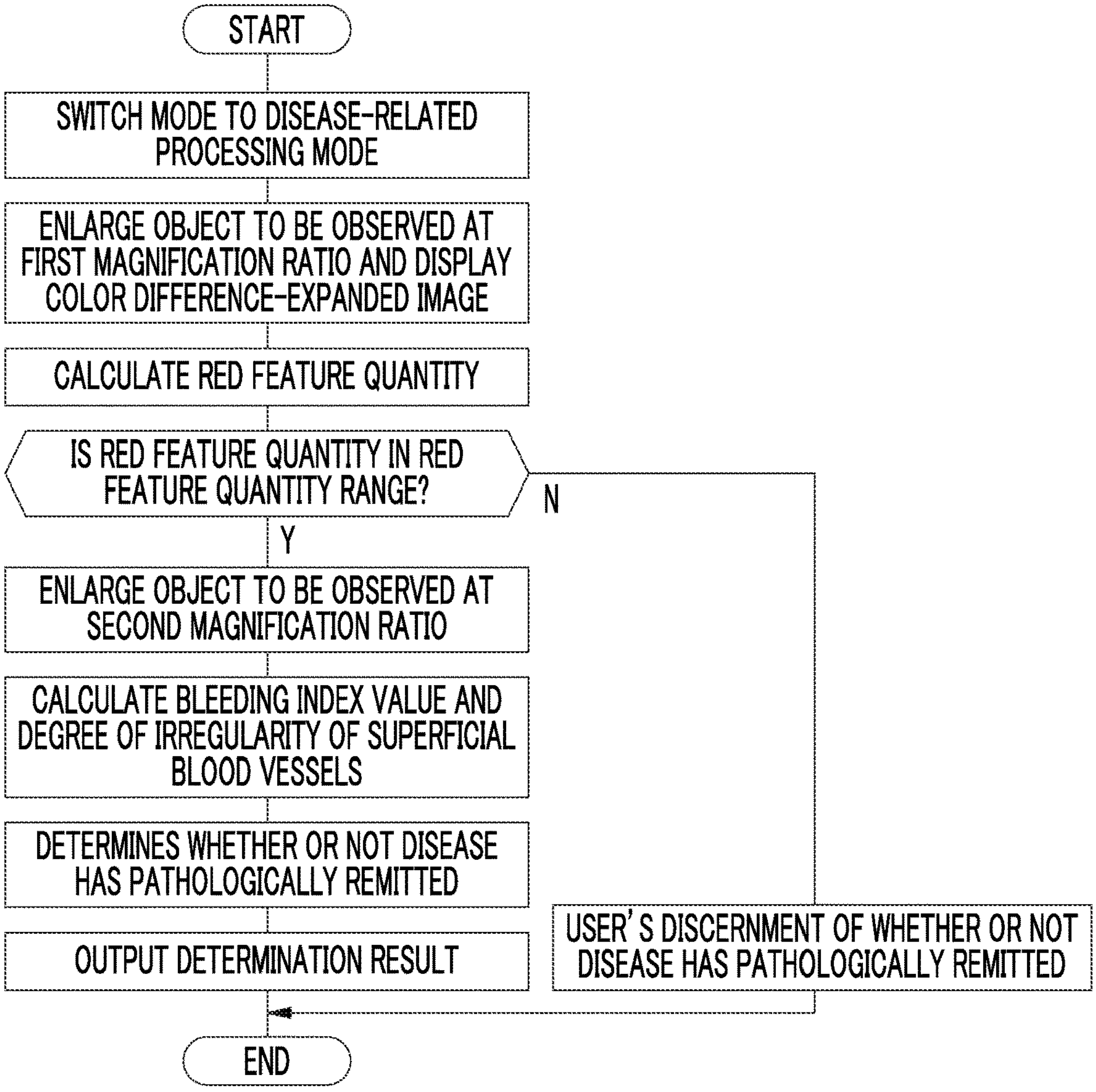
FIG. 21 is a flowchart showing a series of flows of a disease-related processing mode.

Next, a series of flows of a disease-related processing mode will be described with reference to a flowchart shown in FIG. 21. In a case where a user operates the mode changeover SW 12*f* to switch a mode to the disease-related processing mode, an environment in which an object to be observed is observed is set to the first observation environment. In the first observation environment, the object to be observed is enlarged at the first magnification ratio and is illuminated with special light. Further, the color difference-expanded image obtained from illumination using special light and the color difference expansion processing is displayed on the display 18 in the first observation environment. It is preferable that the first observation environment is automatically or manually set.

The switching determination index value-calculation unit 86 calculates a red feature quantity as the switching determination index value on the basis of the color difference-expanded image. In a case where the red feature quantity is out of the red feature quantity range (in a case where the red feature quantity is smaller than the lower limit Lx or is equal to or larger than the upper limit Ux), the switching determination unit 87 determines that switching to the second observation environment is not to be performed. In this case, a user determines whether or not a disease has pathologically remitted.

On the other hand, in a case where the red feature quantity is in the red feature quantity range, the switching determination unit 87 determines that switching to the second observation environment is to be performed. The observation environment switching unit 88 sets the magnification ratio of the object to be observed to the second magnification ratio by a specific operation and switches the first observation environment to the second observation environment. In the second observation environment, illumination using special light is performed as in the first observation environment but display is switched to the special light image from the color difference-expanded image on the display 18.

The remission determination index value-calculation section 90*a* calculates the bleeding index value or the degree of irregularity of superficial blood vessels on the basis of the special light image. In a case where the bleeding index value is equal to or smaller than the threshold value for bleeding and the degree of irregularity of superficial blood vessels is equal to or smaller than the threshold value for the degree of irregularity, the remission determination section 90*b* determines that a disease has pathologically remitted. On the other hand, in a case where the bleeding index value exceeds the threshold value for bleeding or the degree of irregularity of superficial blood vessels exceeds the threshold value for the degree of irregularity, the remission determination section 90*b* determines that the disease has not pathologically remitted. The determination result of the remission determination section 90*b* is displayed on the display 18.

Second Embodiment

In a second embodiment, an object to be observed is illuminated using a broadband light source, such as a xenon lamp, and a rotary filter instead of the four color LEDs 20*a* to 20*d* described in the first embodiment. Further, the image of the object to be observed is picked up by a monochrome image pickup sensor instead of the color image pickup sensor 44. Others are the same as those of the first embodiment.

Figure 22:
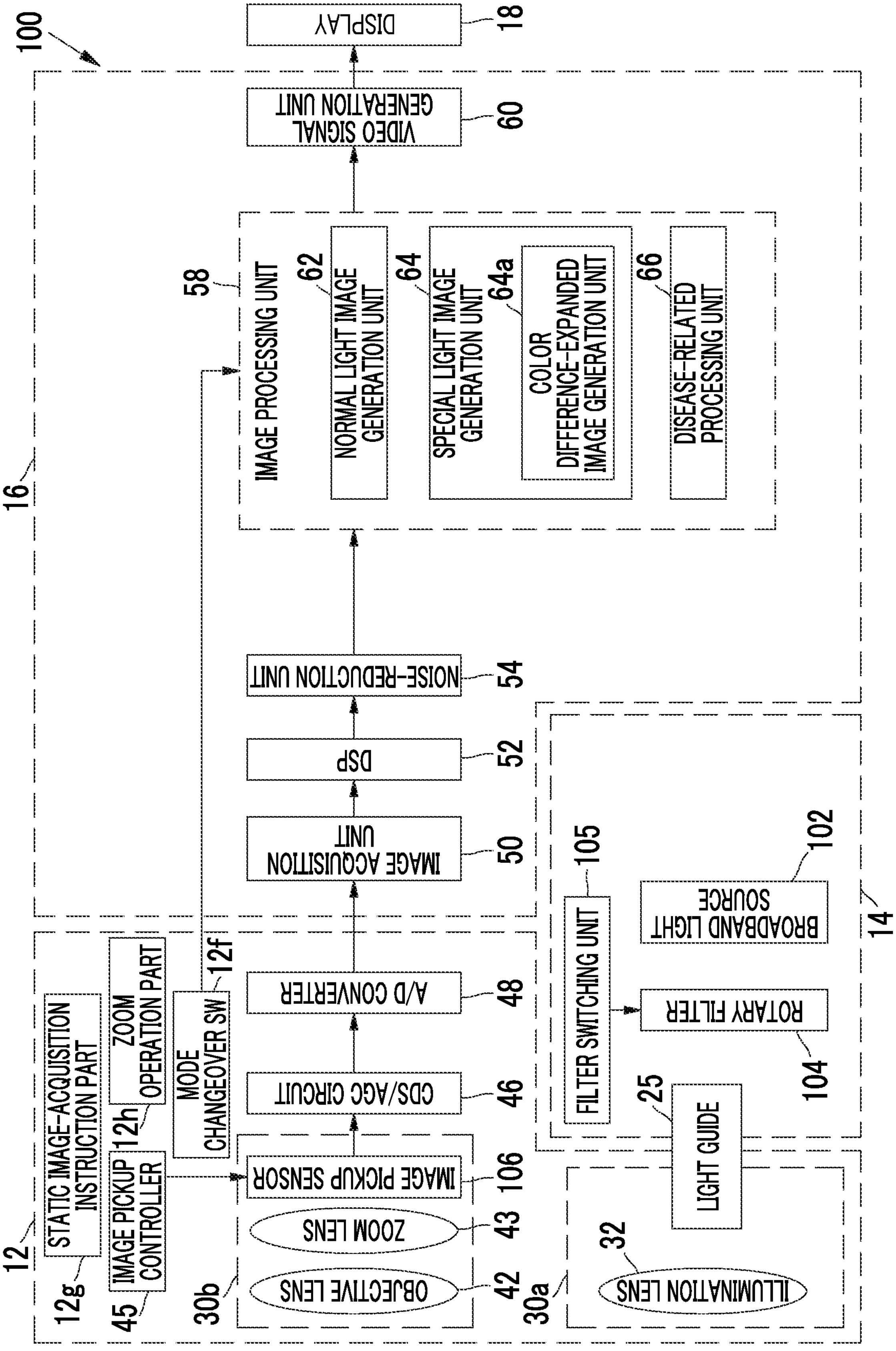
FIG. 22 is a block diagram showing the functions of an endoscope system according to a second embodiment.

As shown in FIG. 22, in an endoscope system 100 according to the second embodiment, a light source device 14 is provided with a broadband light source 102, a rotary filter 104, and a filter switching unit 105 instead of the four color LEDs 20*a* to 20*d*. Further, an image pickup optical system 30*b* is provided with a monochrome image pickup sensor 106, which is not provided with a color filter, instead of the color image pickup sensor 44.

The broadband light source 102 is a xenon lamp, a white LED, or the like, and emits white light of which the wavelength range reaches the wavelength range of red light from the wavelength range of blue light. The rotary filter 104 is provided with a filter 107 for normal light and a filter 108 for special light that are arranged in this order from the inside (see FIG. 23). The filter switching unit 105 is to move the rotary filter 104 in a radial direction, inserts the filter 107 for normal light into the optical path of white light in a case where the endoscope system 100 is set to the normal light mode by the mode changeover SW 12*f*, and inserts the filter 108 for special light into the optical path of white light in a case where the endoscope system 100 is set to the special light mode or the disease-related processing mode.

Figure 23:
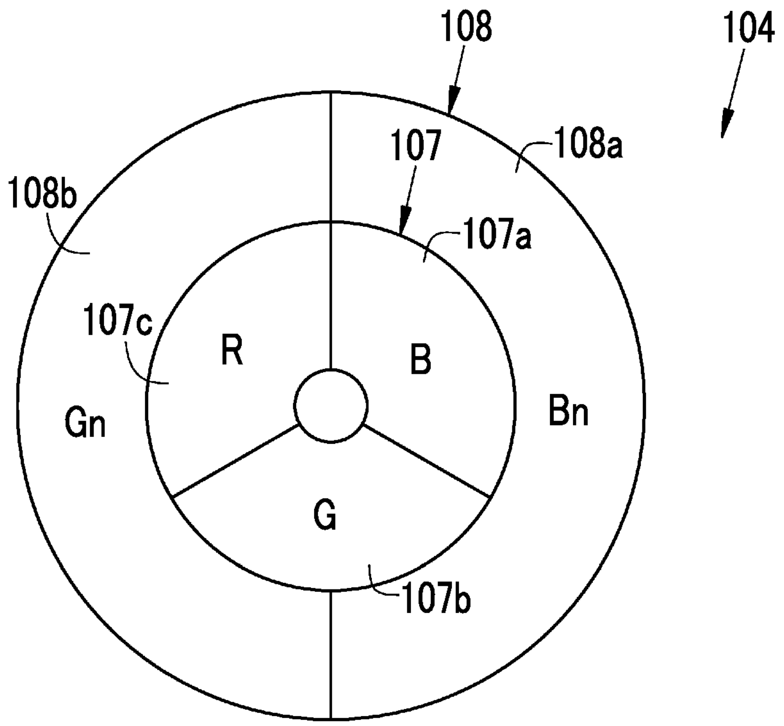
FIG. 23 is a plan view of a rotary filter.

As shown in FIG. 23, the filter 107 for normal light is provided with a B-filter 107*a*, a G-filter 107*b*, and an R-filter 107*c* that are arranged in a circumferential direction. The B-filter 107*a* transmits broadband blue light B of white light, the G-filter 107*b* transmits broadband green light G of white light, and the R-filter 107*c* transmits broadband red light R of white light. Accordingly, in the normal light mode, the rotary filter 104 is rotated to allow the object to be observed to be alternately irradiated with broadband blue light B, broadband green light G, and broadband red light R as normal light.

The filter 108 for special light is provided with a Bn-filter 108*a* and a Gn-filter 108*b* that are arranged in the circumferential direction. The Bn-filter 108*a* transmits narrow-band blue light of white light, and the Gn-filter 108*b* transmits narrow-band green light of white light. Accordingly, in the special light mode or the disease-related processing mode, the rotary filter 104 is rotated to allow the object to be observed to be alternately irradiated with narrow-band blue light and narrow-band green light, which are narrow-band light having a short wavelength, as special light. It is preferable that the wavelength range of the narrow-band blue light is in the range of 400 to 450 nm and the wavelength range of the narrow-band green light is in the range of 540 to 560 nm.

In the endoscope system 100, the image of the object to be observed is picked up by the monochrome image pickup sensor 106 whenever the object to be observed is illuminated with broadband blue light B, broadband green light G, and broadband red light R in the normal light mode. Accordingly, Bc-image signals, Gc-image signals, and Rc-image signals are obtained. Then, a normal light image is generated on the basis of these three-color image signals by the same method as the first embodiment.

In the endoscope system 100, the image of the object to be observed is picked up by the monochrome image pickup sensor 106 whenever the object to be observed is illuminated with narrow-band blue light and narrow-band green light in the special light mode or the disease-related processing mode. Accordingly, Bs-image signals and Gs-image signals are obtained. Then, a special light image is generated on the basis of these two-color image signals by the same method as the first embodiment.

Third Embodiment

In a third embodiment, an object to be observed is illuminated using a laser light source and a phosphor instead of the four color LEDs 20*a* to 20*d* described in the first embodiment. Only portions different from those of the first embodiment will be described below and the description of substantially the same portions as those of the first embodiment will be omitted.

Figure 24:
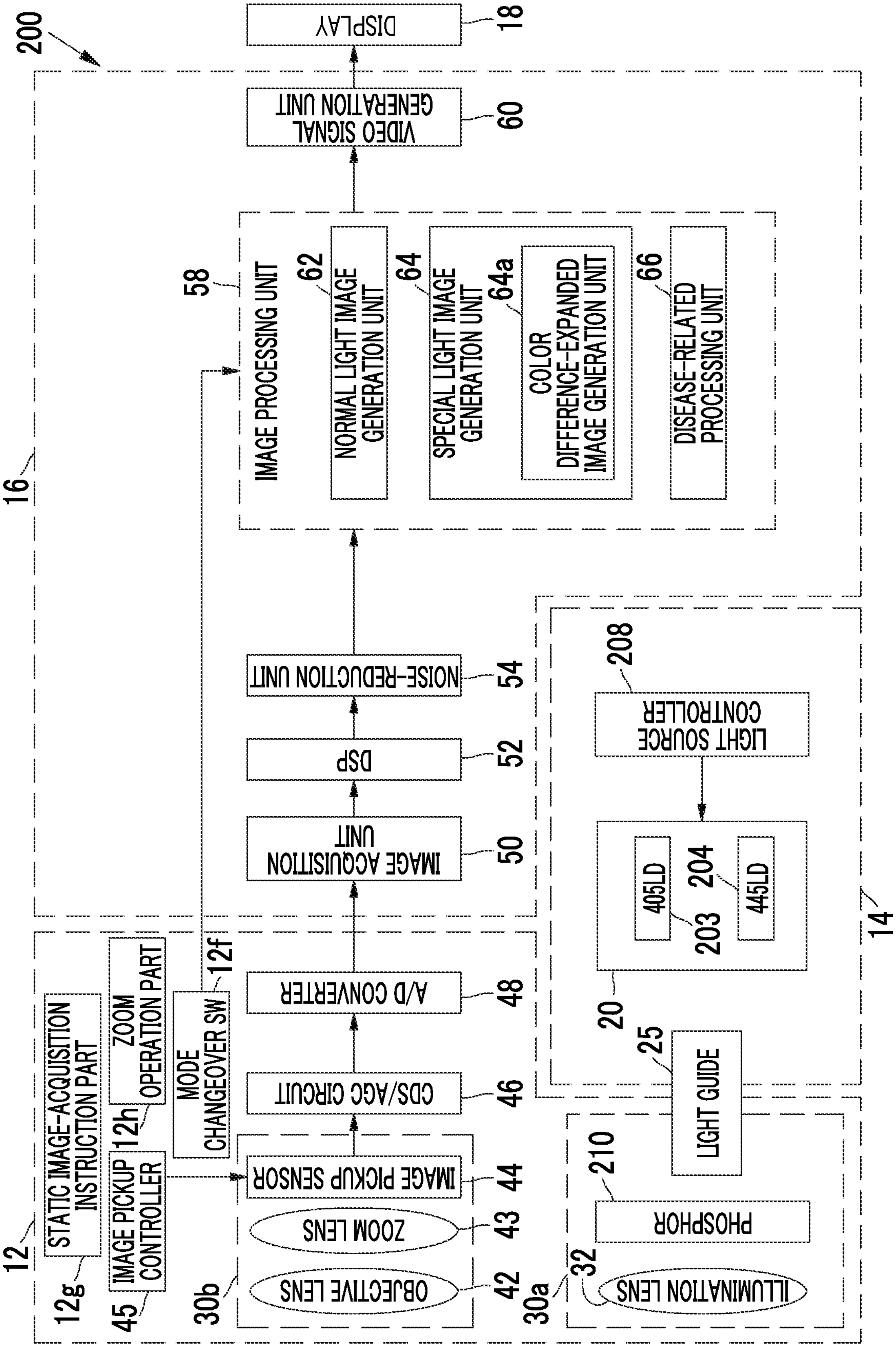
FIG. 24 is a block diagram showing the functions of an endoscope system according to a third embodiment.

As shown in FIG. 24, in an endoscope system 200 according to the third embodiment, a light source unit 20 of a light source device 14 is provided with a violet laser light source unit 203 (written as "405LD". LD represents "Laser Diode") emitting violet laser light of which the central wavelength is in the range of 405±10 nm and a blue laser light source unit (written as "445LD") 204 emitting blue laser light of which the central wavelength is in the range of 445±10 nm, instead of the four color LEDs 20*a* to 20*d*. The violet laser light and the blue laser light correspond to narrow-band light having a short wavelength. The emission of light from semiconductor light-emitting elements of these respective light source units 203 and 204 is individually controlled by a light source controller 208.

The light source controller 208 turns on the blue laser light source unit 204 in the case of the normal light mode. In contrast, the light source controller 208 simultaneously turns on the violet laser light source unit 203 and the blue laser light source unit 204 in the case of the special light mode or the disease-related processing mode.

It is preferable that the half-width of violet laser light or blue laser light is set to about ±10 nm. Further, a broad area-type InGaN-based laser diode can be used as the violet laser light source unit 203 or the blue laser light source unit 204, and an InGaNAs-based laser diode or a GaNAs-based laser diode can also be used. Furthermore, a light emitter, such as a light emitting diode, may be used as the light source.

The illumination optical system 30*a* is provided with a phosphor 210 on which violet laser light or blue laser light emitted from the light guide 25 is to be incident in addition to the illumination lens 32. The phosphor 210 is excited by blue laser light and emits fluorescence. Accordingly, blue laser light corresponds to excitation light. Further, a part of blue laser light is transmitted without exciting the phosphor 210.

Figure 25:
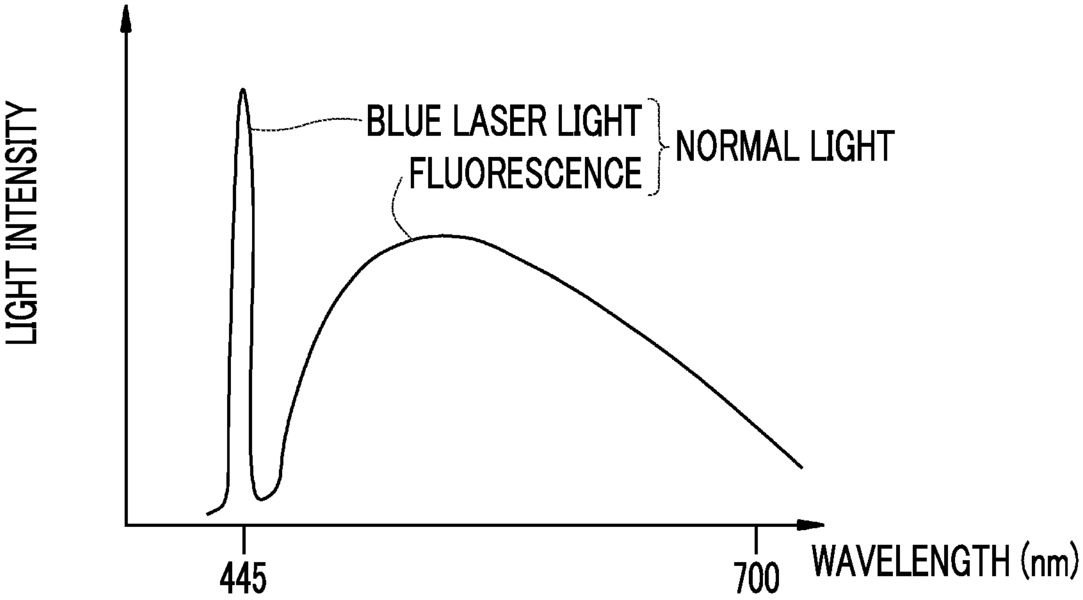
FIG. 25 is a graph showing the spectrum of normal light of the third embodiment.

Here, since blue laser light is mainly incident on the phosphor 210 in the normal light mode, the object to be observed is illuminated with normal light in which blue laser light and fluorescence, which is excited and emitted from the phosphor 210 by blue laser light, are multiplexed as shown in FIG. 25. The image of the object to be observed illuminated with this normal light is picked up by the image pickup sensor 44, so that a normal light image consisting of Bc-image signals, Gc-image signals, and Rc-image signals is obtained.

Figure 26:
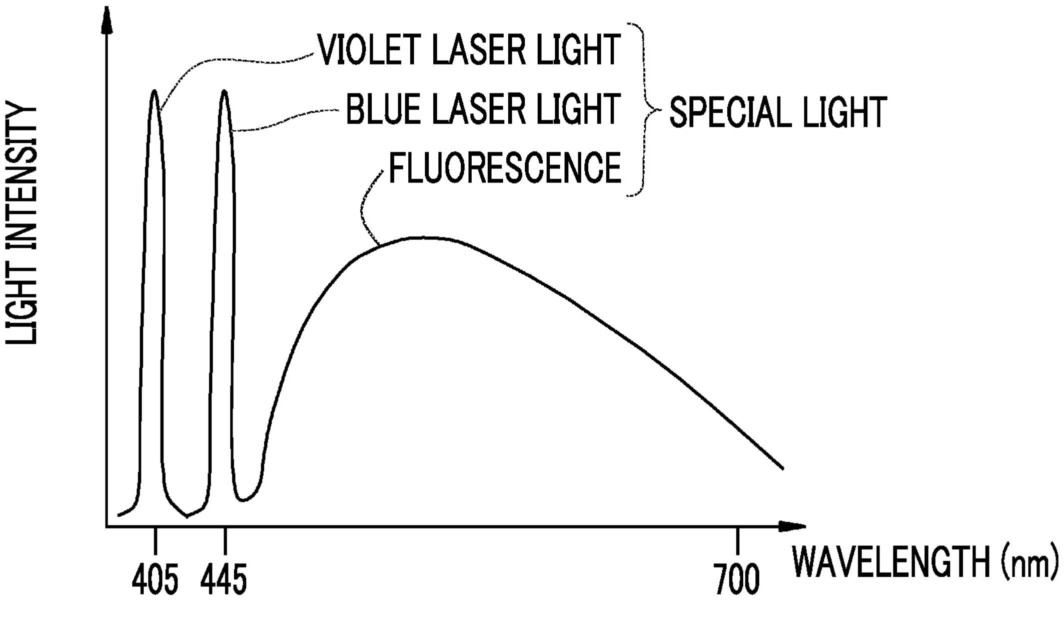
FIG. 26 is a graph showing the spectrum of special light of the third embodiment.

Further, violet laser light and blue laser light are simultaneously incident on the phosphor 210 in the special light mode or the disease-related processing mode, so that pseudo-white light, which includes fluorescence excited and emitted from the phosphor 210 by violet laser light and blue laser light in addition to violet laser light and blue laser light, is emitted as special light as shown in FIG. 26. The image of the object to be observed illuminated with this special light is picked up by the image pickup sensor 44, so that a special light image consisting of Bs-image signals, Gs-image signals, and Rs-image signals is obtained. Pseudo-white light may be light in which violet light V, blue light B, green light G, and red light emitted from the V-LED 20*a*, the B-LED 20*b*, the G-LED 20*c*, and the R-LED 20*d* are combined.

It is preferable that a phosphor including a plurality of types of phosphors absorbing a part of blue laser light and excited by green to yellow light to emit light (for example, YKG-based phosphors or phosphors, such as BAM ($BaMgAl_{10}O_{17}$)) is used as the phosphor 210. In a case where the semiconductor light-emitting elements are used as the excitation light source of the phosphor 210 as in this example of configuration, high-intensity white light is obtained with high luminous efficacy and not only the intensity of white light can be easily adjusted but also a change in the color temperature and chromaticity of white light can be suppressed to be small.

The present invention has been applied to the endoscope system for processing an endoscopic image, which is one of medical images, in the embodiments, but the present invention can also be applied to medical image processing systems for processing medical images other than an endoscopic image. Further, the present invention can also be applied to a diagnosis support device for providing diagnostic support to a user using a medical image. Furthermore, the present invention can also be applied to a medical service support device for supporting a medical service, such as a diagnostic report, using a medical image.

Figure 27:
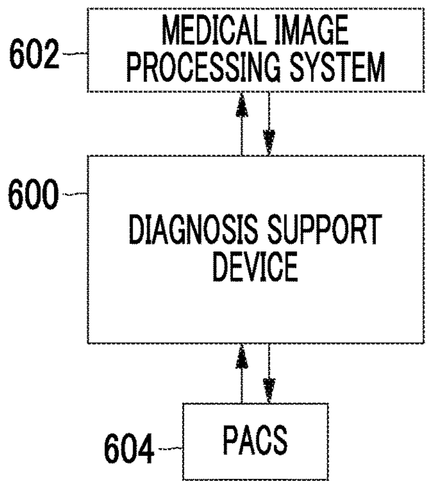
FIG. 27 is a block diagram showing a diagnosis support device.
Figure 28:
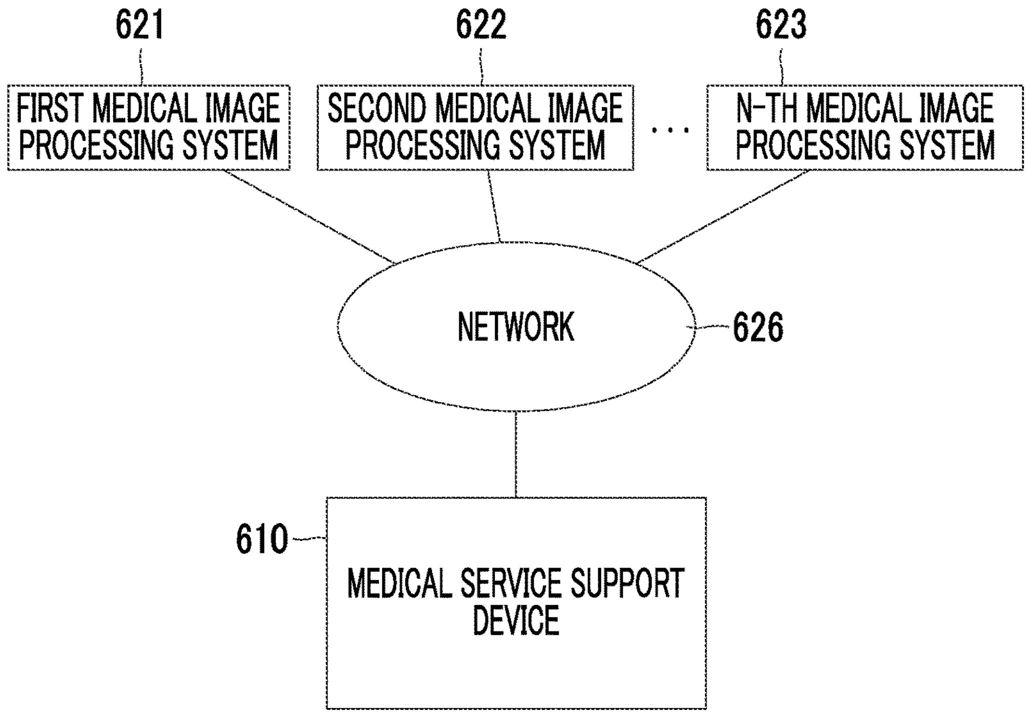
FIG. 28 is a block diagram showing a medical service support device.

For example, as shown in FIG. 27, a diagnosis support device 600 is used in combination with the modality of a medical image processing system 602 or the like and a picture archiving and communication system (PACS) 604. Further, as shown in FIG. 28, a medical service support device 610 is connected to various inspection apparatuses, such as a first medical image processing system 621, a second medical image processing system 622, . . . , and an N-th medical image processing system 623, through an arbitrary network 626. The medical service support device 610 receives medical images from the first to N-th medical image processing systems 621, 622, . . . , and 623, and supports a medical service on the basis of the received medical images.

The hardware structures of the processing units, which are included in the image processing unit 58 in the embodiments and execute various types of processing, such as the normal light image generation unit 62, the special light image generation unit 64, the color difference-expanded image generation unit 64*a*, the disease-related processing unit 66, the reverse gamma conversion section 70, the Log transformation section 71, the signal ratio calculation section 72, the polar coordinate transformation section 73, the color difference expansion section 74, the chroma saturation enhancement processing section 76, the hue enhancement processing section 77, the Cartesian coordinate transformation section 78, the RGB conversion section 79, the brightness adjustment section 81, the structure enhancement section 82, the inverse Log transformation section 83, the gamma conversion section 84, the switching determination index value-calculation unit 86, the switching determination unit 87, the observation environment switching unit 88, the processing execution unit 90, the remission determination index value-calculation section 90*a*, and the remission determination section 90*b*, are various processors to be described below. The various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various types of processing; and the like.

One processing unit may be formed of one of these various processors, or may be formed of a combination of two or more same type or different types of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by a system-on-chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disc drive (HDD) or a solid state drive (SSD).

The present invention can also be embodied by another embodiment to be described below.

A processor device uses a switching determination index value-calculation unit to calculate a switching determination index value, which is used to determine whether or not to switch a first observation environment to a second observation environment in which an object to be observed is enlarged at a second magnification ratio higher than a first magnification ratio, on the basis of a first medical image that is obtained from the image pickup of the object to be observed in the first observation environment in which the object to be observed is enlarged at the first magnification ratio;

uses a switching determination unit to determine whether or not to switch the first observation environment to the second observation environment on the basis of the switching determination index value;

uses an observation environment switching unit to set a magnification ratio of the object to be observed to the second magnification ratio by a specific operation and to switch the first observation environment to the second observation environment in a case where it is determined that switching to the second observation environment is to be performed; and uses a processing execution unit to perform disease state processing, which is related to the state of a disease, on the basis of a second medical image that is obtained from the image pickup of the object to be observed in the second observation environment.

EXPLANATION OF REFERENCES

10: endoscope system
12: endoscope
12*a*: insertion part
12*b*: operation part
12*c*: bendable part
12*d*: distal end part
12*e*: angle knob
12*f*: mode changeover switch
12*g*: static image-acquisition instruction part
12*h*: zoom operation part
14: light source device
16: processor device
18: display
19: user interface
20: light source unit
20*a*: V-LED
20*b*: B-LED
20*c*: G-LED
20*d*: R-LED
21: light source controller
23: optical path-combination unit
25: light guide
30*a*: illumination optical system

30*b*: image pickup optical system
32: illumination lens
42: objective lens
43: zoom lens
44: image pickup sensor
45: image pickup controller
46: CDS/AGC circuit
47: magnification ratio display section
48: A/D converter
49: magnification ratio display section
49*a*: horizontally long bar
49*b*: upper limit display bar
50: image acquisition unit
52: DSP
54: noise-reduction unit
58: image processing unit
60: video signal generation unit
62: normal light image generation unit
64: special light image generation unit
64*a*: color difference-expanded image generation unit
66: disease-related processing unit
70: reverse gamma conversion section
71: Log transformation section
72: signal ratio calculation section
73: polar coordinate transformation section
74: color difference expansion section
76: chroma saturation enhancement processing section
77: hue enhancement processing section
78: Cartesian coordinate transformation section
79: RGB conversion section
81: brightness adjustment section
81*a*: first brightness information-calculation section
81*b*: second brightness information-calculation section
82: structure enhancement section
83: inverse Log transformation section
84: gamma conversion section
86: switching determination index value-calculation unit
87: switching determination unit
88: observation environment switching unit
90: processing execution unit
90*a*: remission determination index value-calculation section
90*b*: remission determination section
100: endoscope system
102: broadband light source
104: rotary filter
105: filter switching unit
106: image pickup sensor
107: filter for normal light
107*a*: B-filter
107*b*: G-filter
107*c*: R-filter
108: filter for special light
108*a*: Bn-filter
108*b*: Gn-filter
200: endoscope system
203: violet laser light source unit
204: blue laser light source unit
208: light source controller
210: phosphor
600: diagnosis support device
602: medical image processing system
604: PACS
610: medical service support device
621: first medical image processing system
622: second medical image processing system
623: N-th medical image processing system
626: network

What is claimed is:

1. An endoscope system comprising:

a light source device configured to emit normal light and special light each having different spectral characteristics;

an endoscope having an image pickup optical system including an objective lens and a zoom lens, the image pickup optical system being configured to change a magnification ratio of an object to be observed; and a processor configured to:

control the light source device and the image pickup optical system to obtain a first medical image of the object to be observed in a first observation environment in which the object to be observed is enlarged at a first magnification ratio and illuminated with the normal light;

calculate a switching determination index value, which is used to determine whether or not to switch the first observation environment to a second observation environment in which the object to be observed is enlarged at a second magnification ratio higher than the first magnification ratio and illuminated with the special light, on the basis of the first medical image;

determine whether the switching determination index value is within a predetermined range; and control the light source device and the image pickup optical system (i) to maintain the first observation environment when the switching determination index value is not within the predetermined range, and (ii) to switch from the first observation environment to the second observation environment by automatically operating the light source device and the image pickup optical system when the switching determination index value is within the predetermined range wherein the switching determination index value is a red feature quantity representing a red component of the object to be observed, the red feature quantity being a number of pixels in a red image of the first medical image comprising pixels, each of the pixels being counted as part of the number of pixels when a red pixel value of each of the pixels is equal to or greater than a predetermined red threshold value.

2. The endoscope system according to claim 1, wherein the processor determines that switching to the second observation environment is not to be performed in a case where the red feature quantity is smaller than a lower limit of a red feature quantity range or a case where the red feature quantity is equal to or larger than an upper limit of the red feature quantity range, and determines that switching to the second observation environment is to be performed in a case where the red feature quantity is in the red feature quantity range.

3. The endoscope system according to claim 1, wherein the first observation environment includes illuminating the object to be observed with normal light or special light or displaying a color difference-expanded image in which a color difference in a plurality of ranges to be observed of the object to be observed expands on a display, and the second observation environment includes illuminating the object to be observed with special light.

4. The endoscope system according to claim 1, wherein the first magnification ratio is less than 60 times and the second magnification ratio is 60 times or more.

5. The endoscope system according to claim 1, wherein the processor is further configured to perform disease state processing, which is related to a state of a disease, on the basis of a second medical image obtained from image pickup of the object to be observed in the second observation environment, and the disease state processing includes at least one of calculating an index value related to a stage of the disease, determining the stage of the disease, or determining whether or not the disease has pathologically remitted on the basis of the second medical image.

6. The endoscope system according to claim 5, wherein the processor is further configured to:

calculate a bleeding index value, which represents a degree of bleeding of the object to be observed, or a degree of irregularity of superficial blood vessels; and determine whether or not the disease has pathologically remitted on the basis of the bleeding index value or the degree of irregularity of the superficial blood vessels.

7. The endoscope system according to claim 6, wherein the processor determines that the disease has pathologically remitted in a case where the bleeding index value is equal to or smaller than a threshold value for bleeding and the degree of irregularity of the superficial blood vessels is equal to or smaller than a threshold value for the degree of irregularity, and determines that the disease has not pathologically remitted in a case where any one of a condition in which the bleeding index value exceeds the threshold value for bleeding or a condition in which the degree of irregularity of the superficial blood vessels exceeds the threshold value for the degree of irregularity is satisfied.

8. The endoscope system according to claim 6, wherein the bleeding index value is a second number of pixels having pixel values equal to or smaller than a threshold value for blue in a blue image of the second medical image, and the degree of irregularity is the second number of pixels of a region in which a density of the superficial blood vessels included in the second medical image is equal to or higher than a threshold value for density.

9. The endoscope system according to claim 5, wherein the disease is ulcerative colitis.

10. A method of operating an endoscope system that includes a light source device configured to emit normal light and special light each having different spectral characteristics and an endoscope having an image pickup optical system including an objective lens and a zoom lens, the image pickup optical system being configured to change a magnification ratio of an object to be observed, the method comprising:

a step of controlling the light source device and the image pickup optical system to obtain a first medical image of the object to be observed in a first observation environment in which the object to be observed is enlarged at a first magnification ratio and illuminated with the normal light;

a step of calculating a switching determination index value, which is used to determine whether or not to switch the first observation environment to a second observation environment in which the object to be observed is enlarged at a second magnification ratio higher than the first magnification ratio and illuminated with the special light, on the basis of a first medical image;

a step of determining whether the switching determination index value is within a predetermined range; and a step of controlling the light source device and the image pickup optical system (i) to maintain the first observation environment when the switching determination index value is not within the predetermined range, and (ii) to switch from the first observation environment to the second observation environment by automatically operating the light source device and the image pickup optical system when the switching determination index value is within the predetermined range, wherein the switching determination index value is a red feature quantity representing a red component of the object to be observed, the red feature quantity being a number of pixels in a red image of the first medical image comprising pixels, each of the pixels being counted as part of the number of pixels when a red pixel value of each of the pixels is equal to or greater than a predetermined red threshold value.

* * * * *